(12) United States Patent
Tedder et al.

(10) Patent No.: US 9,814,740 B2
(45) Date of Patent: Nov. 14, 2017

(54) METHODS AND COMPOSITIONS COMBINING IMMUNOTHERAPY WITH MONOCYTE ACTIVATION

(75) Inventors: Thomas Tedder, Durham, NC (US); Mayuka Horikawa, Durham, NC (US)

(73) Assignee: Duke University, Durham, NC (US)

( * ) Notice: Subject to any disclaimer, the term of this patent is extended or adjusted under 35 U.S.C. 154(b) by 321 days.

(21) Appl. No.: 13/996,307

(22) PCT Filed: Dec. 21, 2011

(86) PCT No.: PCT/US2011/066487
§ 371 (c)(1),
(2), (4) Date: Jul. 22, 2013

(87) PCT Pub. No.: WO2012/088272
PCT Pub. Date: Jun. 28, 2012

(65) Prior Publication Data
US 2013/0309244 A1 Nov. 21, 2013

Related U.S. Application Data

(60) Provisional application No. 61/425,383, filed on Dec. 21, 2010.

(51) Int. Cl.
| | | |
|---|---|---|
| *A61K 39/395* | (2006.01) | |
| *A61K 31/713* | (2006.01) | |
| *C07K 16/28* | (2006.01) | |
| *A61K 39/00* | (2006.01) | |

(52) U.S. Cl.
CPC ........ *A61K 31/713* (2013.01); *A61K 39/3955* (2013.01); *A61K 39/39558* (2013.01); *C07K 16/2803* (2013.01); *C07K 16/2887* (2013.01); *A61K 2039/505* (2013.01); *C07K 2317/73* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,298,614 A | 3/1994 | Yano | |
| 6,780,429 B1 | 8/2004 | Matsuyama et al. | |
| 7,438,907 B2 * | 10/2008 | Schuurman | A61K 39/3955 424/133.1 |
| 7,534,772 B2 * | 5/2009 | Weiner | A61K 39/39541 424/130.1 |
| 7,695,716 B2 * | 4/2010 | Drachman | A61K 39/3955 424/133.1 |
| 2004/0265315 A1 * | 12/2004 | Dingivan | C07K 16/2806 424/155.1 |
| 2006/0120997 A1 * | 6/2006 | Lipton | 424/85.2 |
| 2008/0253998 A1 | 10/2008 | Andre et al. | |
| 2009/0074711 A1 * | 3/2009 | Glennie | A61K 38/164 424/85.2 |
| 2009/0123467 A1 | 5/2009 | Bedi et al. | |
| 2010/0266680 A1 | 10/2010 | Andre et al. | |
| 2011/0135666 A1 | 6/2011 | Tedder et al. | |
| 2012/0183535 A1 * | 7/2012 | Buggy | A61K 31/195 424/133.1 |
| 2013/0136754 A1 | 5/2013 | Tedder et al. | |
| 2014/0065118 A1 | 3/2014 | Tedder et al. | |

FOREIGN PATENT DOCUMENTS

| | | | | |
|---|---|---|---|---|
| FR | WO 2008025848 A2 * | 3/2008 | ........... | A61K 38/164 |
| WO | WO 98/23761 | 6/1998 | | |
| WO | WO 9823761 A1 * | 6/1998 | ......... | C07K 16/2845 |
| WO | WO 98/50547 | 11/1998 | | |
| WO | WO 0110462 A1 * | 2/2001 | | |
| WO | WO 2004/053452 | 6/2004 | | |
| WO | WO 2004/053057 | 10/2004 | | |
| WO | WO 2005000901 | 1/2005 | | |
| WO | WO 2006/121852 | 11/2006 | | |
| WO | WO 2008/025848 | 3/2008 | | |
| WO | WO 2009/131712 | 10/2009 | | |
| WO | WO 2009126819 A1 * | 10/2009 | | |
| WO | WO 2010/132659 | 11/2010 | | |
| WO | WO 2010132659 A2 * | 11/2010 | ......... | C07K 16/2893 |

(Continued)

OTHER PUBLICATIONS

Weitzman et al., Blood. Aug. 15, 1990;76(4):655-63.*
Federico et al., Int J Cancer. Dec. 1, 2007;121 (11 ):2381-6.*
Parsonnet, J., Environ Health Perspect. Nov. 1995;103 Suppl 8:263-8.*
Maini et al., Arthritis Res. 2002;4 Suppl 2:S22-8. Epub Mar. 27, 2002.*
Cang et al., J Hematol Oncol. Oct. 11, 2012;5:64. doi: 10.1186/1756-8722-5-64.*

(Continued)

*Primary Examiner* — Michael Szperka

(74) *Attorney, Agent, or Firm* — Andrus Intellectual Property Law, LLP

(57) ABSTRACT

Methods of enhancing the effectiveness of an antibody-based therapeutic agent are provided herein. The methods include administering an antibody-based therapeutic and a composition capable of preferentially activating monocytes or macrophages or preferentially depleting B10 cells to a subject in need of such treatment. The subject may have cancer, an autoimmune disease, an infectious disease or an immunodeficiency. The composition capable of preferentially activating monocytes or macrophages may be a TLR3 agonist. The composition capable of preferentially depleting B10 cells may be a CD19 antibody. Pharmaceutical compositions comprising an antibody-based therapeutic agent and a composition capable of preferentially activating monocytes or macrophages or preferentially depleting B10 cells are also provided.

8 Claims, 28 Drawing Sheets

(56) References Cited

FOREIGN PATENT DOCUMENTS

WO WO 2012/019041 2/2012

OTHER PUBLICATIONS

El Zouhairi et al., Gastrointest Cancer Res. Jan. 2011;4(1):15-21.*
Ozoya et al., J Clin Transl Hepatol. Jun. 28, 2016;4(2):143-50. doi: 10.14218/JCTH.2016.00005. Epub Jun. 15, 2016.*
Ai et al., J Rheumatol. Dec. 2015;42(12):2229-37. doi: 10.3899/jrheum.150057. Epub Oct. 15, 2015.*
Adachi, O. et al., "Targeted disruption of the MyD88 gene results in loss of IL-1- and IL-18-mediated function," (1998) Immunity 9, 143-150.
Anolik, J. H. et al., "New treatments for SLE: Cell-depleting and anti-cytokine therapies," 2005 Best Practice & Research Clinical Rheumatology 19(5):859-878.
Ben-Kasus, T. et al., "Cancer therapeutic antibodies come of age: Targeting minimal residual disease," (2007) Molecular Oncology 1:42-54.
Blair, P.A. et al., "CD19+CD24hiCD38h cells exhibit regulatory capacity in healthy individuals but are functionally impaired in systemic lupus erythematosus patients," 2010 Immunity 32:129-140.
Brummel, R. et al., "Activation of Marginal Zone B Cells from Lupus Mice with Type A(D) CpG-Oligodeoxynucleotides1," 2005 J. Immunol. 174:2429-34.
DiLillo, D. J. et al., "B10 cells and regulatory B cells balance immune responses during inflammation, autoimmunity, and cancer," Ann. N. Y. Acad. Sci. 1183, 38-57 (2010).
Fillatreau S., "Novel regulatory functions for Toll-like receptor-activated B cells during intracellular bacterial infection," Immunol. Rev. 240, 52-71 (2011).
Haas, K. M. et al., "CD22 ligand binding regulates normal and malignant B lymphocyte survival In Vivo," (2006) J. Immunol. 177:3063-3073.
Haas, K. M. et al., "Protective and pathogenic roles for B cells during systemic autoimmunity in NZB/W F1 mice," J. Immunol. 184, 4789-4800 (2010).
Hamaguchi, Y. et al., "The peritoneal cavity provides a protective niche for B1 and conventional B lymphocytes during anti-CD20 immunotherapy in mice," (2005) J. Immunol 174, 4389-4399.
Hasegawa, M. et al., "B-lymphocyte depletion reduces skin fibrosis and autoimmunity in the tight-skin mouse model for systemic sclerosis," 2006, Am. J. Pathol. 169:954-66.
Horikawa, M. et al., "Regulatory B cell production of IL-10 inhibits lymphoma depletion during CD20 immunotherapy in mice," J. Clin. Invest. 121, 4268-4280 (2011).
Huang, J. et al., "Isolation of human monoclonal antibodies from peripheral blood B cells," (2013) Nature Protocols 8(10):1907-1915.
Inoue, S. et al., "Inhibitory effects of B cells on antitumor immunity," 2006 Cancer Res. 66:7741-7747.
International Search Report and Written Opinion in International Patent Application No. PCT/US2011/066487 dated May 2, 2012 (10 pages).
Iwata, Y. et al., "Characterization of a rare IL-10-competent B cell subset in humans that parallels mouse regulatory B10 cells," Blood 117, 530-541 (2011).
Kawai, T. et al., "Unresponsiveness of MyD88-deficient mice to endotoxin," (1999) Immunity 11, 115-122.
Levesque, M.C. et al., "B cell-directed therapies for autoimmune disease and correlates of disease response and relapse," 2008 J. Allergy Clin. Immunol. 121:13-21.
Matsushita, et al., "B-lymphocyte depletion for the treatment of multiple sclerosis: Now things really get interesting," 2009 Expert Rev. Neurotherapeutics 9(3):309-312.
Matsushita, et al., "Inhibitory role of CD19 in the progression of experimental autoimmune encephalomyelitis by regulating cytokine response," 2006 Am. J. Path., 168(3):812-821.

Matsushita, T. et al., "Regulatory B cells (B10 cells) and regulatory T cells have independent roles in controlling EAE initiation and late-phase immunopathogenesis," J. Immunol. 185, 2240-2252 (2010).
Minard-Colin, V. et al., "Lymphoma depletion during CD20 immunotherapy in mice is mediated by macrophage FcγRI, FcγRIII, and FcγRIV," (2008) Blood 112, 1205-1213.
Poe. J. C. et al., "Amplified B lymphocyte CD40 signaling drives regulatory B10 cell expansion in mice," (2011) PLoS ONE 6, e22464.
Uchida. J. et al., "The innate mononuclear phagocyte network depletes B lymphocytes through Fc receptor-dependent mechanisms during anti-CD20 antibody immunotherapy," (2004a) J Exp Med 199, 1659-1669.
Yanaba. K. et al., "A regulatory B cell subset with a unique CDIdhiCD5+ phenotype controls T cell-dependent inflammatory responses," Immunity 28, 639-650 (2008).
Yanaba, K. et al., "The development and function of regulatory B cells expressing IL-10 (B10 cells) requires antigen receptor diversity and TLR signals," (2009) J Immunol 182. 7459-7472.
Ai, J., et al., The risk of tuberculosis in patients with rheumatoid arthritis treated with tumor necrosis factor-a antagonist: a meta-analysis of both randomized controlled trials and registry/cohort studies, J Rheumatology, 2015, pp. 2229-2237, vol. 4:12.
Bouaziz, J.D., et al., "Regulatory B cells as inhibitors of immune responses and inflammation," 2008 Immunol. Rev. 224:201-214.
Cang, S., et al., Novel CD20 monoclonal antibodies for lymphoma therapy, Journal of Hematology and Oncology, 2012, 5:64.
Colliou, N. et al., "Long-Term Remissions of Severe Pemphigus After Rituximab Therapy Are Associated with Prolonged Failure of Desmoglein B Cell Response," Science Translational Medicine 5, 175ra30 (2013).
Dzhagalov, I. et al., "The antiapoptotic protein Mcl-1 is essential for the survival of neutrophils but not macrophages," (2007) Blood 109, 1620-1626.
El Zouhairi, M., et al., Molecularly targeted therapy for metastatic colon cancer: proven treatments and promising new agents, Gastrointest. Cancer Res., 2011, 15-21, 4:1.
Fillatreau, S. et al., "B cells regulate autoimmunity by provision of IL-10," Nat. Immunol. 3, 944-950 (2002).
Goodnow, C.C. et al., Altered immunoglobulin expression and functional silencing of self-reactive B lymphocytes in transgenic mice, Nature, 1988, pp. 676-682, vol. 334.
Haas, K. M. et al., "B-1a and B-1b cells exhibit distinct developmental requirements and have unique functional roles in innate and adaptive immunity to S. pneumoniae," 2005, Immunity 23:7-18.
Harris, D.P. et al., "Reciprocal regulation of polarized cytokine production by effector B and T cells," 2000, Nat. Immunol. 1:475-82.
Hayakawa, I. et al., "B-lymphocyte depletion ameliorates Sjogren's syndrome in Id3 knockout mice," 2007, Immunology 122:73-9.
Huggins, J. et al., "CpG DNA activation and plasma-cell differentiation of CD27_naïve human B cells," Blood 109(4):1611-1619 (2007).
Kandimalla, E.R., et al., Divergent synthetic nucleotide motif recognition pattern: design and development of poten immunomodulatory oligodeoxyribonucleotide agents with distinct cytokine induction profiles, (2003) Nucl. Acid. Res. 31(9): 2393-2400.
Kurosaki, T., "Paradox of B cell-targeted therapies," 2008 J. Clin. Inv. 118(10):3260-3263.
Lampropoulou, V. et al., "TLR-activated B cells suppress T cell-mediated autoimmunity," 2008 J. Immunol. 180:4763-4773.
Lebien, T. W., and Tedder, T. F., B-lymphocytes: How they develop and function. Blood, 2008, pp. 1570-1579, vol. 112.
Lund, et al., "Cytokine-producing B lymphocytes—key regulators of immunity," 2008 Curr. Op. Immunol. 20(3):332-338.
Lyons, J.-A. et al., "B cells are critical to induction of experimental allergic encephalomyelitis by protein but not by a short encephalitogenic peptide," 1999 Eur. J. Immunol. 29:3432-3439.
Maini, R.N., et. al., How does infliximab work in rheumatoid arthritis, Arthritis Res., 2002, 4 Supp 2:S22-8.

(56) References Cited

OTHER PUBLICATIONS

Matsushita, T. et al., "Identifying regulatory B cells (B10 cells) that produce IL-10," Methods Mol. Biol. 677, 99-111 (2011).
Mauri, C. et al., "The 'short' history of regulatory B cells," 2008, TRENDS in Immunol. 29: 34-40.
Mauri C., "Regulation of immunity and autoimmunity by B cells," Curr. Opin. Immunol. 22, 761-7657 (2010).
Ozoya, O.O., et al., Hepatitis B reactivation with novel agentsin non-hodgin's lymphoma and prevention strategies, J Clinical and Translation Hepatology, 2016, pp. 143-150, vol. 4.
Wehr, C., et al., A new CD21low B cell population in the peripheral blood of patients with SLE, Clin. Immunol., 2004, pp. 161-171, vol. 113.2.
Xiu, Y. et al., "B lymphocyte depletion by CD20 monoclonal antibody prevents diabetes in nonobese diabetic mice despite isotype-specific differences in FcγR effector funcitons," 2008, J. Immunol. 180:2863-75.
Yanaba, K. et al., "B cell depletion delays collagen-induced arthritis in mice: Arthritis induction requires synergy between humoral and cell-mediated immunity," 2007, J. Immunol. 179:1369-80.
Yanaba, K. et al., "Regulatory B cells," 2009 Jap. Soc. Clin. Immunol. 32(3):135-141 (Abstract).
International Search Report and Written Opinion in International Patent Application No. PCT/US2009/002560 dated Jul. 20, 2010 (10 pages).
International Search Report and Written Opinion in International Patent Application No. PCT/US2011/046643 dated Mar. 14, 2012 (11 pages).

\* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA CpG
<220> FEATURE:
<221> NAME/KEY: misc_feature
<222> LOCATION: (1)..(3)
<223> OTHER INFORMATION: Phosphorothioate
<220> FEATURE:
<221> NAME/KEY: misc_feature
<222> LOCATION: (17)..(19)
```

```
<223> OTHER INFORMATION: Phosphorothioate

<400> SEQUENCE: 1
tccatgacgt tcctgatgct                                                    20
```

METHODS AND COMPOSITIONS COMBINING IMMUNOTHERAPY WITH MONOCYTE ACTIVATION

CROSS-REFERENCE TO RELATED APPLICATIONS.

This patent application is a national stage filling under 35 U.S.C 371 of International Application No. PCT/US2011/066487, filed Dec. 21, 2011, which claims the benefit of priority of U.S. Provisional Patent Application No. 61/425,383, filed Dec. 21, 2010, both of which are incorporated herein by reference in their entirety.

STATEMENT REGARDING FEDERALLY SPONSORED RESEARCH

This invention was made with United States government support awarded by the National Institutes of Health grant numbers AI56363 and AI057157. The United States may have certain rights in this invention.

REFERENCE TO SEQUENCE LISTING SUBMITTED VIA EFS-WEB

This application is being filed electronically via EFS-Web and includes an electronically submitted Sequence listing in .txt format. The .txt file contains a sequence listing entitled "2012-02-21_5667-00085_Sequence—Listing_as_Filed .txt" created on Feb. 21, 2012 and is 627 bytes in size. The Sequence Listing contained in this .txt file is part of the specification and is hereby incorporated by reference herein in its entirety.

INTRODUCTION

Immunotherapeutics, in particular antibody-based therapeutics, are being developed to treat many diseases including cancer and autoimmune diseases. Many antibody-based therapeutics bind to cell-surface expressed molecules and target cancer cells or autoimmune cells for destruction. The targeted cells may be destroyed by antibody-dependent cell-mediated cytotoxicity (ADCC). In many cases, immunotherapy with antibody-based therapeutics is only partially effective and must be combined with other more traditional therapeutics to effectively treat the disease. Thus, a better understanding of why antibody-based therapeutics are not more effective and development of additional therapies that may enhance the effectiveness of the antibody-based therapeutics are needed.

SUMMARY

Methods of treatment for a subject having a condition amenable to treatment with an antibody-based therapeutic are provided herein. In one aspect, the methods of treatment include administering an antibody-based therapeutic agent and a composition to a subject in need thereof. The composition is capable of preferentially activating monocyte or macrophage cells relative to the effect of the composition on a B10 cell or capable of preferentially depleting or deactivating B10 cells relative to monocyte or macrophage cells. The composition capable of preferentially activating a monocyte or macrophage cell may be a TLR3 (toll-like receptor) agonist. The composition capable of preferentially depleting or deactivating B10 cells may be a CD19 antibody. The subject may be in need of treatment for cancer, an autoimmune disease, an inflammatory disease, an infectious disease or an immunodeficiency.

In yet another aspect, pharmaceutical compositions comprising an antibody-based therapeutic and a composition capable of preferentially activating monocyte or macrophage cells relative to B10 cells or capable of preferentially depleting or deactivating B10 cells relative to monocytes or macrophages are provided. The composition capable of preferentially activating a monocyte or macrophage cell may be a TLR3 agonist. The composition capable of preferentially depleting or deactivating a B10 cell may be a CD19 antibody.

DESCRIPTION OF THE DRAWINGS

FIG. 1 is a set of graphs showing that endogenous B cells inhibit lymphoma depletion by CD20 mAb in vivo. In FIGS. 1B and 1E significant differences between means are indicated; *p<0.05, **p<0.01.

FIG. 2 is a set of graphs showing that B10 cell production of IL-10 inhibits lymphoma killing by CD20 mAb in vivo. (FIGS. 2A and 2C) Significant differences between means are indicated, *p<0.05, **p<0.01.

FIG. 3 is a set of graphs showing that B10 cells inhibit macrophage activation.

FIG. 4 is a set of graphs showing that TLR agonists induce monocyte activation and enhance CD20 mAb-induced B cell depletion. In FIG. 4C-E significant differences between sample means are indicated; *p<0.05, **p<0.01. Results represent 3-4 independent experiments.

FIG. 5 is a set of graphs showing that poly I:C enhances BL3750 lymphoma depletion by CD20 mAb. In FIGS. 5B-F significant differences between sample means, or mice treated with CD20 mAb alone compared with CD20 mAb plus poly I:C are indicated; *p<0.05, **p<0.01. In FIGS. 5B and D at time points where insufficient numbers of mice treated with control mAb had not survived for statistical analysis, comparisons were made between mice treated with both CD20 mAb plus poly I:C versus pooled results for viable mice treated with either CD20 mAb or poly I:C alone.

FIG. 6 is a set of graphs showing that poly I:C does not induce B10 cell proliferation or IL-10 production. In FIG. 6B-F the results represent ≥2 independent experiments.

FIG. 7 is a set of graphs showing that TLR3 activation enhances CD20 and CD19 mAb immunotherapy for lymphoma. In FIGS. 7A-C, mice were given BL3750 cells one day before isotype control mAb (○, 250 µg), or CD20 or CD19 mAb (●, 250 µg) treatments, with poly I:C (□, 150 µg) administered on days 1, 7, 14, 21. Significant differences between sample means, or mice treated with mAb alone or mAb plus poly I:C are indicated; *p<0.05, **p<0.01. At time points where insufficient numbers of mice treated with control mAb had not survived, statistical comparisons were made between mice treated with both CD20/CD19 mAb plus poly I:C versus pooled results for viable mice treated with either CD20 or isotype control mAb alone.

DETAILED DESCRIPTION

Figure 1A:
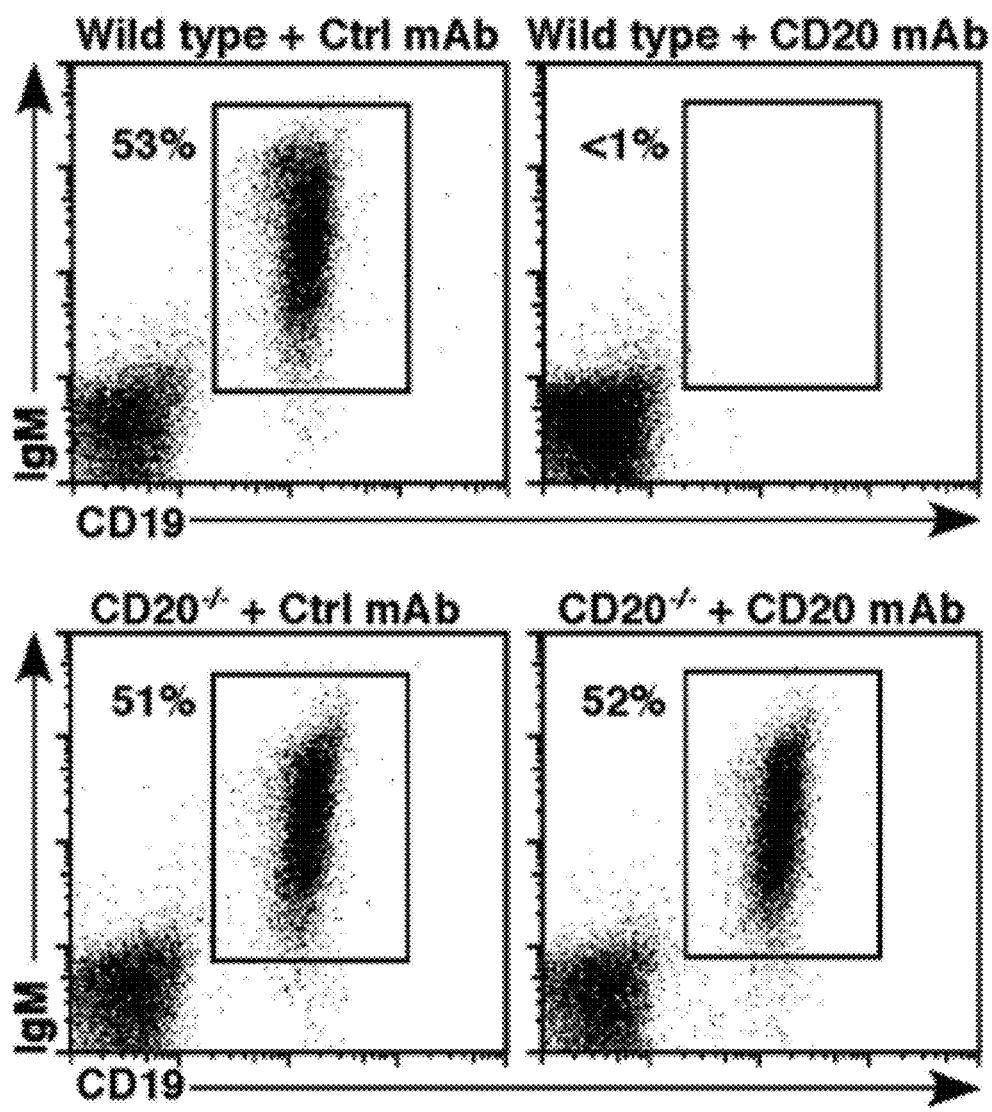
FIG. 1A shows B cells in $CD20^{-/-}$ mice are resistant to CD20 mAb-induced depletion. Results show representative circulating $IgM^+CD19^+$ B cell percentages in wild type or $CD20^{-/-}$ mice 7 days after control or CD20 mAb treatment (250 µg/mouse). Identical results were also obtained 6 days after control or CD20 mAb treatment in mice given $10^6$ BL3750 cells 1 day before mAb treatment (data not shown). Percentages indicate the relative frequencies of cells within the indicated gates. Results are representative of 4 independent experiments.

Methods of enhancing the effectiveness of an antibody-based therapeutic agent are provided herein. The methods of treatment provided include administering an antibody-based therapeutic agent and a composition capable of selectively and/or preferentially activating monocytes or macrophages relative to B10 cells or a composition capable of selectively and/or preferentially deactivating or depleting B10 cells but not monocytes or macrophages to a subject in need of such treatment. The subject is an individual, suitably a mammal, suitably a human in need of treatment for a condition or disease treatable with an antibody-based therapeutic agent. The subject may have cancer, an autoimmune disease, an inflammatory disease, an infectious disease or an immunodeficiency. As shown in the Examples, administration of an antibody-based therapeutic agent and a composition capable of preferentially activating monocyte/macrophage cells or depleting B10 cells enhances the effectiveness of the antibody-based therapeutic agent by decreasing the subject's resistance to the antibody-based therapeutic agent and increasing the inhibitory effect of the antibody-based therapeutic agent on disease progression.

Without being limited to a particular mechanism of action, the inventors believe that the administration of a composition capable of preferentially activating cells of the macrophage/monocyte lineage to a subject being treated with an antibody-based therapeutic agent will increase the effectiveness of the antibody-based therapeutic agent by enhancing antibody-dependent cell-mediated cytotoxicity (ADCC) of the cells targeted by the antibody-based therapeutic agent. Increased ADCC of cancer cells or autoimmune cells targeted by an antibody-based therapeutic agent will result in quicker, more efficient clearance of these cells and ameliorate the disease or symptoms of the disease more effectively than administration of the antibody-based therapeutic agent alone. The efficacy of antibody-based therapeutic agents may be limited by regulatory cells, such as B10 cells, which serve to limit the immune clearance of the targeted cells. Administration of a composition capable of preferentially activating cells of the macrophage/monocyte lineage, as compared to regulatory B10 cells, overcomes the inhibitory effect of these regulatory cells and increases the efficacy of the treatment. In general, the antibody-based therapeutic agent will target cells other than those of the macrophage/monocyte lineage.

An antibody-based therapeutic agent refers to any therapeutic or prophylactic agent with an $F_c$ portion of an antibody and a second portion capable of binding to a target as part of the structure of the therapeutic. The $F_c$ portion of the therapeutic is capable of binding to the $F_c$ receptor on an immune effector cell (e.g., NK cell, or cell of the macrophage or monocyte lineage) in order to mediate clearance of the target. The $F_c$ receptor is preferably an $F_{c\gamma}$ receptor. Thus, antibody-based therapeutic agents may also be called $F_{c\gamma}$R-dependent therapeutics. The target may be a protein, a carbohydrate, a nucleic acid, a lipid, a cell, a tissue or any combination thereof (i.e. a lipoprotein or a glycoprotein). The second portion of the therapeutic agent which is capable of binding the target may be a $F_{ab}$ portion of an antibody or a ligand for a cell-surface receptor. Antibody-based therapeutic agents include, but are not limited to, monoclonal antibodies, polyclonal antibodies, humanized antibodies, genetically engineered antibodies, or hybrid, chimeric or fusion proteins including an $F_c$ portion of an antibody.

Many antibody-based therapeutic agents have been described in the literature and many others are currently under development. Examples of antibody-based therapeutic agents include, but are not limited to agents that target or mediating binding to CD20, ErbB-2, CD33, CD52, VEGF, EGFR, VEGFR-2, RANKL, TRAIL-1, CD4, VEGF-A, CD25, CTLA-4, CD64, CA-125, EpCam, CD40, PEM, mesothelin, CD11a, CD2, CD19, CD22, TNF-α, α4 integrin and IL-6R. In the Examples, an antibody specific for CD20 is used and its efficacy is increased by administration with a TLR3 agonist, specifically poly (I:C). Those of skill in the art will appreciate that antibody-based therapeutic agents having additional specificities may also be used in the methods.

Those of skill in the art will also appreciate that fusion proteins could be developed in which a polypeptide encoding the $F_c$ portion of an antibody is fused to a polypeptide capable of binding to a target molecule. The target molecule may be any molecule, such as a nucleic acid, protein, carbohydrate or lipid which is expressed by cells associated with the disease or condition for which the subject needs treatment. For example, the target molecule may be differentially expressed or over-expressed on cells associated with the disease or condition, such as cancer cells, or activated immune cells. The target molecule may be a viral or pathogen protein expressed on infected cells and not found on uninfected cells. Those of skill in the art will appreciate that such antibody-based therapeutic agents may be genetically engineered to target a particular disease.

The antibody-based therapeutic agent may be useful for treatment of various diseases. Suitably, the antibody-based therapeutic agent is directed for treatment of cancer, an autoimmune disease, an infectious disease, an inflammatory disease or an immunodeficiency. In one embodiment, the subject is in need of treatment for cancer. The cancer may be a solid, non-lymphoid tumor, or a tumor of epithelial origin, such as breast cancer, colorectal cancer, head and neck cancer, stomach cancer, renal cancer, lung cancer, ovarian cancer, prostate cancer, and brain cancer. The cancer may be a leukemia or a lymphoma including leukemias, such as but not limited to, acute leukemia, acute lymphocytic leukemia, acute myclocytic leukemias such as myeloblastic, promyclocytic, myelomonocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease, and multiple myelomas. The subject may be in need of treatment for an autoimmune disease. The autoimmune disease may be selected from, but is not limited to alopecia areata, ankylosing spondylitis, autoimmune arthritis including rheumatoid arthritis, Addison's disease, hemolytic anemia, autoimmune thrombocytopenic purpura, Behcet's disease, autoimmune cardiomyopathy. Celiac disease, Crohn's disease, Diabetes mellitus type I, autoimmune epilepsy, Kawasaki's disease, Graves' disease, Goodpasture's syndrome, Guillain-Barre Syndrome, Inflammatory Bowel Disease, Lupus nephritis, Multiple Sclerosis, Myasthenia gravis, autoimmune myocarditis, Parkinsons disease, pemphigus, Sjögren's disease, systemic lupus erythematosus, and others. The subject may be in need of treatment for an inflammatory disease such as arthritis. The subject may be in need of treatment for an infectious disease such as a viral, bacterial, fungal or parasitic disease. The subject may be in need of treatment for an immunodeficiency such as HIV-mediated immunodeficiency, or immunodeficiency due to immune-suppressive therapy.

The composition capable of preferentially activating a monocyte or macrophage cell is a composition capable of activating macrophages and monocytes without also activating other immune cells, in particular without activating B cells and T cells. Suitably, the composition preferentially activates macrophages and/or monocytes as compared to B10 cells. Suitably, the composition is capable of activating monocytes and macrophages with-out activating regulatory cells, such as B10 cells. As described in the Examples below one such composition capable of selectively activating cells of the monocyte/macrophage lineage without also activating B10 cells is a TLR3 agonist. In the Examples, the TLR3 agonist used was poly (I:C). Suitably, the TLR3 agonists are those that activate TRIF-dependent signaling pathways.

TLR3 agonists are affinity agents (i.e., a molecule that binds a target molecule) capable of activating a TLR3 polypeptide to induce a full or partial receptor-mediated response. For example, an agonist of TLR3 induces TLR3-mediated signaling, either directly or indirectly. A TLR3 agonist, as used herein, may but is not required to bind a TLR3 polypeptide, and may or may not interact directly with the TLR3 polypeptide. For example, a TLR3 agonist also includes agonists which activate TLR3-mediated signaling without necessarily interacting with the TLR3 polypeptide.

Toll Like Receptor 3 (TLR3, CD283) is a member of the Toll-like receptor (TLR) family which plays a fundamental role in pathogen recognition and activation of innate immunity. TLRs are highly conserved from *Drosophila* to mice to humans and share structural and functional similarities. They recognize pathogen-associated molecular patterns (PAMPs) that are expressed on infectious agents, and mediate the production of cytokines necessary for the development of effective immunity. TLR3 is most abundantly expressed in placenta and pancreas, and is restricted to the monocyte, macrophage and dendritic subpopulations of the leukocytes. It recognizes dsRNA associated with viral infection, and induces the activation of NF-kappaB and the production of type I interferons. It may thus play a role in host defense against viruses. TLR3 mRNA sequence is described in NCBI accession number NM003265, the sequence of which is incorporated herein by reference. TLR3 is described in WO 98/50547 (the disclosure of which is incorporated herein by reference in its entirety).

The TLR3 agonists can be selected from any suitable agent. For example, TLR3 agonists can be selected from a range of nucleic acid agonists; other agonists, whether nucleic acid based, proteinaceous or small molecules, can be tested using known assays. For example, assays for detecting TLR3 agonists are described in PCT Publication Nos. WO 03/31573, WO 04/053057, WO 04/053452, and WO 04/094671, the disclosures of which are incorporated herein by reference. Regardless of the particular assay employed, a compound can be identified as a TLR3 agonist if performing the assay with the compound results in at least a threshold increase of some biological activity mediated by TLR3. Conversely, a compound may be identified as not acting as a TLR3 agonist if when used in an assay designed to detect a biological activity mediated by TLR3, the compound fails to elicit a threshold increase in the biological activity. Unless otherwise indicated, an increase in biological activity refers to an increase in the same biological activity over that observed in an appropriate control. An assay may or may not be performed in conjunction with the appropriate control. With experience, one skilled in the art may develop sufficient familiarity with a particular assay (e.g., the range of values observed in an appropriate control under specific assay conditions) that performing a control may not always be necessary to determine the TLR3 agonism of a compound in a particular assay. The precise threshold increase of TLR3-mediated biological activity for determining whether a particular compound is or is not an agonist of TLR3 in a given assay may vary according to factors known in the art including but not limited to the biological activity observed as the endpoint of the assay, the method used to measure or detect the endpoint of the assay, the signal-to-noise ratio of the assay, the precision of the assay and whether the same assay is being used to determine the agonism of a compound for multiple TLRs. Those of ordinary skill in the art, however, can readily determine the appropriate threshold with due consideration of such factors.

The TLR3 agonist can be an isolated and purified natural agonist of a TLR3 or a synthetic TLR3 agonist compound. For example, a TLR3 agonist comprising a nucleic acid molecule can be readily produced in large quantities by one or more standard means known in the art for nucleotide synthesis including, but not limited to, chemical synthesis, enzymatic synthesis, recombinant synthesis, and chemical or enzymatic cleavage from a larger precursor nucleic acid molecule. Synthesis may be in vitro, in vivo, automated, manual, or a combination thereof. In producing a TLR3 agonist, the TLR3 agonist may be purified from other components used in the synthetic process to result in a preparation comprising isolated TLR3 agonist. Deprotection, purification, and analytic methods for nucleic acid molecule synthesis are well known in the art. TLR3 agonists are well known in the art and suitable TLR3 agonists are available. Further TLR3 agonists, or derivatives or analogs of known TLR3 agonists can be readily identified, made and/or assessed. The most commonly used TLR3 agonists are nucleic acid based agonists. Thus a TLR3 agonist for use in the methods and pharmaceutical compositions described herein may be nucleotide or nucleic acid based. The nucleic acid based TLR3 agonist can be single-stranded or double-stranded or a mixture thereof. The nucleic acid based TLR3 agonist can comprise deoxyribonucleotides, or ribonucleotides or a mixture thereof. The nucleotides can be natural or synthetic, and may be derivatives or analogs of natural nucleotides, such as for example those described in Kandimalla et al. ((2003) Nucl. Acid. Res. 31(9): 2393-2400), which is incorporated herein by reference in its entirety.

Double-stranded RNA which represents either genomic or life cycle intermediate material of many viruses activates cells through binding to the dsRNA-dependent protein kinase (PKR), a kinase that initiates a complex molecular anti-viral program. dsRNA triggers the production of type 1 IFN, and dsRNA has been reported to have promise for certain clinical applications such as anti-viral therapies. A dsRNA compound is typically active per se, i.e., they do not encode a polypeptide or do not require translation to be active. dsRNA TLR3 agonists can have any suitable length. Preferably, a dsRNA molecule TLR3 agonist has a length of at least about 10 base pairs (bp), 20 bp, 30 bp, 50 bp, 80 bp, 100 bp, 200 bp, 400 bp, 600 bp, 800 bp or 1000 bp. In another embodiment, the dsRNA molecule is a long dsRNA having a chain length of greater than 1000 bp. In one aspect, a dsRNA composition comprises a heterogenous mixture of dsRNA molecules, wherein a plurality of molecules having differing lengths is used. Suitably in a dsRNA composition comprising a plurality of dsRNA molecules having differing lengths at least 20%, 50%, 80%, 90% or 98% of the dsRNA molecules have a length of at least about 10 bp, 20 bp, 30 bp, 50 bp, 80 bp, 100 bp. 200 bp, 400 bp, 600 bp, 800 bp or 1000 bp. Alternatively, the dsRNA composition has a substantially homogenous mixture of dsRNA molecules, where substantially all the molecules do not differ in chain length by more than 30 bp, 50 bp, 80 bp, 100 bp or 200 bp. Average chain length of nucleic acid TLR3 agonists can be determined easily, for example, by gel permeation chromatography. Each strand of these dsRNAs can have a length comprised between about 5 and 50 bases, more preferably between 5 and 40, 35, 30, 25 or 20 bases. Each strand may be perfectly complementary to the other. Preferred examples of such dsRNAs are homopolyRNAs, i.e., dsRNAs in which each strand comprises essentially a repeat of the same base; or comprise a homopolyRNA region.

Previous studies of double-stranded RNA (dsRNA) assessing their ability to be effective interferon inducers suggested that dsRNA agents must possess the secondary structure of a double stranded helix. Other dsRNA agents which have also been shown to be suitable as TLR3 agonist include double-stranded polynucleotides which are not complementary or not perfectly complementary; these so-called "mismatched" or "loop-out" structures exist in naturally occurring RNAs such as transfer tRNAs, ribosomal RNAs and viral RNA secondary structures. One known dsRNA compound, Ampligen™ (poly I:poly $C_{12}U$; Hemispherx, Inc., of Rockville, Md., U.S.A.), comprises a structure where a few parts of cytidine in the poly I:poly C structure are replaced with uridine (i.e. mismatched RNA); this compound has been reported to have physiological activity similar to that of the parent poly I:poly C, but has lower toxicity. In such a dsRNA uridine can replace one or more cytosines. Suitably, uridine may replace from 1 to 29 cytosines in such a structure. However, it will be appreciated that TLR3 agonists of any type and configuration can be used in accordance with this invention.

The bases may be any naturally occurring base (e.g., polyA, polyU, polyC, polyG) or non-naturally occurring (e.g., chemically synthesized or modified) base (e.g., polyI). Polynucleotides typified by polyinosinic-polycytidylic acid, i.e., poly (I):poly (C) or poly (I:C) and polyadenylic-polyuridylic acid, i.e., poly (A):poly (U) or poly (A:U), are well-known compounds in the art and have been known to induce interferon production by immune cells. Poly (I:C) was used in the Examples. Poly (A:U) was also tested but was not as effective as Poly (I:C) in the mouse model at reducing tumor growth, but poly(A:U)-like molecules may function in the assay. Poly (I:C) like agents such as those including polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue may also be useful. Specific examples of Poly (I:C)-like agents include poly-ICLC, poly I:poly $C_{12}U$ and poly I:mercapto poly C.

It will be appreciated that nucleic acid-based agonists of TLR3 can be designed using any suitable method. Suitably, the stability and resistance to nuclease attack and the preferences for chain length are taken into account. Measures can be taken to increase stability and resistance to nucleases, or to increase or optionally decrease interferon-inducing action.

Other examples of dsRNA include nucleic acids described in U.S. Pat. Nos. 5,298,614 and 6,780,429. U.S. Pat. No. 5,298,614 reports that when chain length of the double stranded nucleic acid derivatives is limited to certain ranges, the resulting substances exhibit desired physiological activity with markedly less toxicity, providing polynucleotides having a length of about 50 to 10,000 as calculated by base pair numbers. Also described are derivatives wherein the purine or pyrimidine ring in the nucleic acid polymer is substituted with at least one SH group, or said derivative contains a disulphide bond, or both (preferred ratio of number of sulphur atoms to cytidylic acid present in the poly C are 1:6 to 39). U.S. Pat. No. 6,780,429 describes a particular type of dsRNA compounds that are "chain-shortened" having lengths of about 100 to 1,000 as calculated by base pair numbers, or preferably from 200 to 800, and more preferably from 300 to 600. The disclosure of each of these references is incorporated herein by reference.

A number of synthetic nucleic acid derivatives have been described, including homopolymer-homopolymer complexes such as those in which poly I:C or poly A:U are a parent structure, where these homopolymer-homopolymer complexes contain: (1) base modifications, exemplified by polyinosinic acid-poly(5-bromocytidylic acid), polyinosinic acid-poly(2-thiocytidylic acid), poly(7-deazainosinic acid)-polycytidylic acid, poly(7-deazainosinic acid)-poly(5-bromocytidylic acid), and polyinosinic acid-poly(5-thiouridylic acid); (2) Sugar Modifications, exemplified by poly(2'-azidoinosinic acid)-polycytidylic acid; and (3) Phosphoric Acid Modifications, exemplified by polyinosinic acid-poly (cytidyl-5'-thiophosphoric acid). Other synthetic nucleic acid derivatives that have been described include interchanged copolymers, exemplified by poly (adenylic acid-uridylic acid); and homopolymer-copolymer complexes, exemplified by polyinosinic acid-poly (cytidylic acid-uridylic acid) and polyinosinic acid-poly (citydylic acid-4-thiouridylic acid). Other synthetic nucleic acid derivatives that have been described include complexes of synthetic nucleic acid with polycations, exemplified by polyinosinic acid-polycytidylic acid-poly-L-lysinecarboxy-methylcellulose complex (poly ICLC). Other examples of synthetic nucleic acid derivatives are polyinosinic acid-poly (1-vinylcytosine) and polyinosinic acid-mercaptopolycytosine.

The TLR3 agonist can also be any organic or inorganic substance, such as a lipid, peptide, polypeptide, small molecule, etc., isolated or in combination with other substances. The TLR3 agonist may be an antibody directed against the TLR3 receptor and which is capable of activating a TLR3 receptor to induce a full or partial receptor-mediated response. The TLR3 agonist can also be an antibody fragment or derivative of an antibody directed against TLR3 receptor and which is capable of activating a TLR3 receptor to induce a full or partial receptor-mediated response.

The composition capable of preferentially deactivating or depleting B10 cells is a composition capable of deactivating or depleting B10 cells without also deactivating or depleting other immune cells, in particular without deactivating or depleting cells of the monocyte/macrophage lineage. Suitably, the composition preferentially deactivates or depletes B10 cells as compared to macrophages and/or monocytes. Deactivation or depletion of B10 cells may occur as a result of killing B10 cells, such as by targeted killing using an antibody specific for a cell surface marker, inhibiting replication or proliferation of B10 cells or inhibiting the ability of B10 cells to produce IL-10. For example, B10 cells may be depleted by selecting an antibody that binds to a marker that is found on B10 cells, including but not limited to, CD5, CD19, CD20, CD21, CD22, CD24, CD40 and CD72. As demonstrated in International Patent Application No. PCT/US2009/002560 (which is incorporated by reference herein in its entirety), CD22 antibodies can be used to preferentially deplete B10 cells. Alternatively, bispecific CD1d/CD5 antibodies may be useful to preferentially deplete B10 cells. Ligands or ligand mimetics of B10 specific markers may also be used to target B10 cells for ablation or deactivation, e.g., by making fusion proteins with an Fc portion of an antibody or conjugating to a cytotoxic agent. Suitably the Fc portion of the antibody mediates either ADCC or complement dependent cytotoxicity of the B10 cells. Those of skill in the art will appreciate that other means can be used to mediate targeted cytotoxicity.

Methods for preventing, managing, treating or ameliorating a disease such as cancer, an autoimmune disease, an inflammatory disease, an infectious disease or an immunodeficiency or one or more symptoms thereof are provided. The methods and compositions described herein provide enhanced efficacy as compared to treatment with the antibody-based therapeutic agent alone. The enhancement in efficacy may result in inhibition of cancer cell or autoimmune cell replication and expansion. Such inhibition is measured in comparison to the growth or replication of untreated, mock treated or control treated subjects. A control treated subject is a subject administered only the antibody-based therapeutic agent.

Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The efficacy of the treatment may be measured in any manner. For example, treatment may result in an inhibition or lessening of adverse symptoms of the disease, may ameliorate the disease, or may cure the disease. For subjects with cancer this may be measured by inhibition of metastases, induction of cancer cell senescence, induction of cancer cell death, reduction of tumor size, reducing progression of a cancer to a more aggressive form, reducing proliferation of cancer cells, reducing the speed of tumor growth, reducing metastasis of cancer cells or reducing the likelihood of recurrence of a cancer in a subject. For a subject with an autoimmune disease or an inflammatory disease, treatment may result in decreased symptoms, decreased frequency of recurrence, or slowing of tissue destruction. For an infectious disease, treatment may result in curing the disease, decreasing the frequency or recurrence or remittance or decreasing symptoms associated with the disease. The combination of the antibody-based therapeutic agent and the composition capable of activating monocyte/macrophage cells or depleting B10 cells described herein may result in death of the target cells by ADCC, induction of apoptosis, inhibition of angiogenesis enhancement of anoikis or inhibition of replication.

An effective amount or a therapeutically effective amount as used herein means the amount of a compound that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated. Suitably the agents are administered in an amount effective to enhance treatment of the disease by increasing clearance from the subject of the diseased cells or blocking proliferation of the diseased cells from the subject such that a therapeutic effect is achieved in the subject.

Administration to a subject in accordance with the methods of the invention may include formulating the therapeutic agents with pharmaceutically acceptable carriers and/or excipients to provide desired dosages, etc., to form pharmaceutical compositions. Suitable formulations for therapeutic compounds are available to those skilled in the art. Administration may be carried out by any suitable method, including but not limited to intraperitoneal, intravenous, intramuscular, intrathecal, subcutaneous, transcutaneous, oral, nasopharyngeal, or transmucosal absorption among others. Thus the compounds may be formulated as an ingestible, injectable, topical or suppository formulation. The compounds may also be delivered with in a liposomal or time-release vehicle. Administration of the compounds to a subject in accordance with the invention appears to exhibit beneficial effects in a dose-dependent manner. Thus, within broad limits, administration of larger quantities of the compounds is expected to achieve increased beneficial biological effects than administration of a smaller amount. Moreover, efficacy is also contemplated at dosages below the level at which toxicity is seen.

The antibody-based therapeutic and the composition capable of activating macrophage/monocyte cells or depleting B10 cells may be administered before, concomitant with or after each other. The antibody-based therapeutic and the macrophage/monocyte activating or B10 depleting composition may be administered concurrently as part of the same pharmaceutical composition or may be administered together as two separate dosage forms via the same or different routes. For example, the antibody-based therapeutic and the first composition may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more. Treatment regimens for given subjects can be determined using conventional considerations, e.g., comparison of the differential activities of the therapeutic agents and of a known agent, such as by means of a conventional therapeutic protocol.

The methods comprise administering to a subject in need thereof a dosage of a prophylactically or therapeutically effective amount of composition capable of preferetially activating cells of the monocyte/macrophage lineage, such as a TLR3 agonist, or a composition capable of preferentially depleting B10 cells, such as a CD22 or CD19 antibody, in combination with the administration of a dosage of a prophylactically or therapeutically effective amount of one or more antibody-based therapeutic agents. Suitably, the TLR3 agonist is a dsRNA compound. Suitably, the composition and the antibody-based therapeutic agent are administered more than once. Optionally, the composition and the antibody-based therapeutic agent are administered at an interval of less than one month, less than three weeks, less than two weeks, or less than one week. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The composition, such as aTLR3 agonist (preferably, a dsRNA) and the antibody-based therapeutic agent may be administered to a subject using a dosing regimen that maintains the plasma concentration of both at a desirable level. The plasma concentration that is desirable in a subject will vary depending on several factors including, but not limited to, the nature of the disease, the severity of the disease, and the circulation half-life (stability) of each compound in the compositions and binding affinity of the composition capable of activating monocyte/macrophages or depleting B10 cells and the antibody-based therapeutic for their targets.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of disease, the route of administration, as well as the age, body weight, general state of health, diet, timing of administration, the rate of excretion and other medicaments being used in combination. Dosages for a given subject can be determined using conventional considerations, e.g., by comparison of the differential activities of the therapeutic agents and of a known agent such as by means of a conventional pharmacological protocol.

The maximal dosage for a subject is the highest dosage that does not cause undesirable or intolerable side effects. The number of variables in regard to an individual treatment regimen is large and a considerable range of doses is expected. The effectiveness of an antibody-based therapeutic agent used in the methods described herein may be enhanced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control treated with the antibody-based therapeutic alone. It will be appreciated that the effectiveness of the treatment in any given case will be affected by the specific compounds used, the type of disease being treated, the condition of the subject, the specific formulations of the compounds and other relevant medical factors that may modify the activity of the therapeutics or the responses of the subject as is appreciated by those of skill in the art.

Suitably, a therapeutically effective amount of a composition capable of activating monocyte/macrophages or depleting B10 cells, such as a TLR3 agonist (in combination with an antibody-based therapeutic agent) reduces the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS or relative to administration of the antibody-based therapeutic agent alone.

The following examples are meant only to be illustrative and are not meant as limitations on the scope of the invention or of the appended claims. All references cited herein are hereby incorporated by reference in their entireties.

EXAMPLES

Experimental Procedures

Mice. $CD20^{-/-}$ mice were as described (Uchida et al., 2004b). C57BL/6 were from uNCI-Frederick Laboratory (Frederick, Md.). $IL-10^{-/-}$ ($B6.129P2-Il10^{tm1Cgn}/J$) and $RagI^{-/-}$ ($B6.129S7-RagI^{tm1Mom}/J$) mice were from the Jackson Laboratory (Bar Harbor, Me.). $Mcl-1^{-/-}$ and WT littermates were as described (Dzhagalov et al., 2007). $Gfi-1^{-/-}$ mice (Hock et al., 2003) were generously provided by H. Hock (Center for Cancer Research, Massachusetts General Hospital, Boston. MA). $MyD88^{-/-}$ mice (Adachi et al., 1998) were provided by S. Akira (Osaka University, Osaka Japan). Mice were housed in a specific pathogen-free barrier facility and first used at 6-10 weeks of age. The Duke University Animal Care and Use Committee approved all studies.

Immunofluorescence analysis. CD20 expression was visualized using biotin-conjugated mouse CD20 (MB20-11) mAb (Uchida et al., 2004b) plus phycoerythrin-Cy5 (PE-Cy5) streptavidin (eBioscience, San Diego, Calif.). Other mAbs included: B220 (RA3-6B2), CD1d (1B1), CD5 (53-

7.3), CD19 (1D3), NK1.1 (PK136), and I-A/I-E (M5/114.15.2) from BD Biosciences (San Jose, Calif.). CD11b (M1/70), CD86 (GL1), F4/80 (BM8), IgM (II/41), Gr-1 (RB6-8C5), and IL-10 (JES5-16E3) mAbs were from eBioscience. TNF-α (MP6-XT22) mAb was from Biolegend (San Diego, Calif.). For immunofluorescence analysis, single cell suspensions ($10^6$ cells) were stained at 4° C. using predetermined optimal concentrations of mAb for 30 minutes as described (Sato et al., 1996).

For IL-10 detection, mouse spleen or blood mononuclear cells, BL3750 tumor cells, or human blood were resuspended ($2 \times 10^6$ cells/ml) in complete medium [RPMI 1640 media (Cellgro, Herndon, Va.) containing 10% FCS (Sigma, St. Louis, Mo.). 200 μg/ml penicillin, 200 U/ml streptomycin. 4 mM L-Glutamine (all Cellgro), and 55 μM 2-mercaptoethanol (Invitrogen, Carlsbad. CA)] with lipopolysaccharide (LPS, 10 μg/ml, *Escherichia coli* serotype 0111: B4, Sigma), phorbol myristate acetate (PMA, 50 ng/ml; Sigma), ionomycin (500 ng/ml; Sigma), and monensin (2 μM; eBioscience) for 5 h. B10 progenitor cells were induced to mature and acquire IL-10 competence in vitro by culturing the cells with LPS (10 μg/ml), CpG (human ODN 2006, 10 μg/ml; Invivogen, San Diego, Calif., mouse ODN 1668, 10 μg/ml; Integrated DNA Technologies, Coralville, Iowa), or poly I:C (Invivogen) for 48 h with the addition of monensin, PMA and ionomycin for the last 5 h of culture. For TNF-α detection, bone marrow cells were resuspended ($2 \times 10^6$ cells/ml) in complete medium with Brefeldin A (1 μl; Biolegend) and TLR agonists (25 μg/ml) for 4 h. Before cell surface staining, Fc receptors were blocked using Fc receptor mAb (2.4G2; BD Biosciences), and dead cells were labeled using a LIVE/DEAD® Fixable Green Dead Cell Stain Kit (Invitrogen-Molecular Probes). Stained cells were fixed and permeabilized using a Cytofix/Cytoperm kit (BD Biosciences) according to the manufacturer's instructions and stained with anti-IL-10 or anti-TNF-α mAbs. Isotype-matched mAbs or splenocytes from IL-10$^{-/-}$ mice served as negative controls for IL-10 staining to demonstrate specificity and to establish background IL-10 staining levels. Isotype-matched mAbs or sample cultured with Brefeldin A only served as negative controls for TNF-α staining. Informed consent for human blood samples was obtained in each instance according to protocols approved by the Institutional Review Board of Duke University Medical Center.

Lymphoma model. BL3750 lymphoma cells were as described (Minard-Colin et al., 2008). This lymphoma model is accepted by those skilled in the art as a standard model for human lymphoma disease. For each experiment, tumor cells were thawed and expanded for 24-48 hours in complete medium (RPMI 1640 media containing 20% fetal bovine serum, 100 U/ml penicillin, 100 μg/ml streptomycin, 2 mM L-glutamine, and 55 μM 2-mercaptoethanol). BL3750 cells in 250 μl PBS were injected subcutaneously into the dorsal skin of recipient mice on day 0. This mouse model of lymphoma is a standard animal model for human lymphoma used and accepted by those skilled in the art. Mice were then given purified mAb in 250 μl of PBS intravenously, and starting on day 7 were monitored daily for tumor development and progression, and survival. Tumor measurements were as described (Minard-Colin et al., 2008). All mice were euthanized when exhibiting distress or tumor volumes exceeding 2.0 cm$^3$ with the date of euthanasia recorded as the date of death from disease.

Figure 3A:
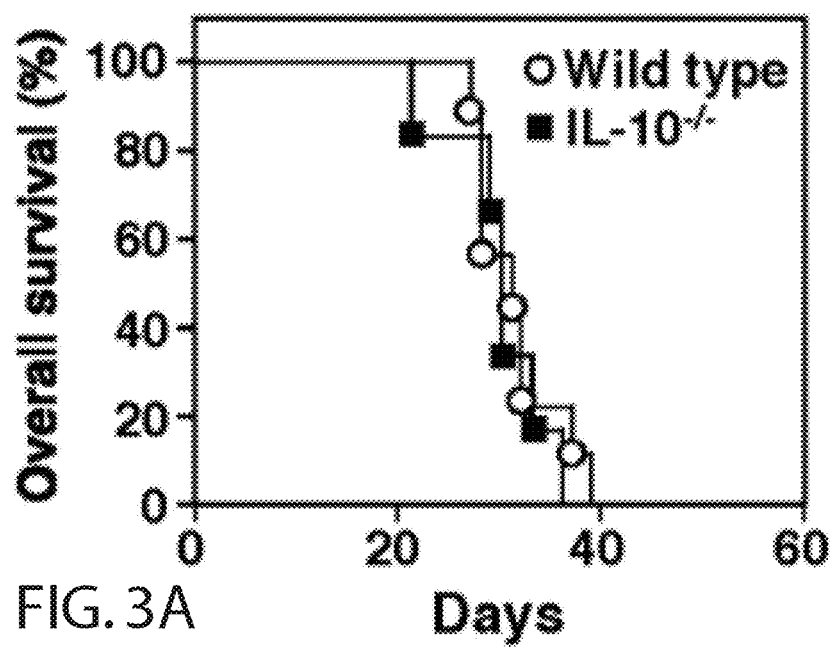
FIG. 3A shows that IL-10 does not influence BL3750 tumor growth in vivo. Wild type and IL-10$^{-/-}$ mice (n=6-9 mice/group) were given 10$^5$ BL3750 (cells on day 0 with survival monitored thereafter.
Figure 3B:
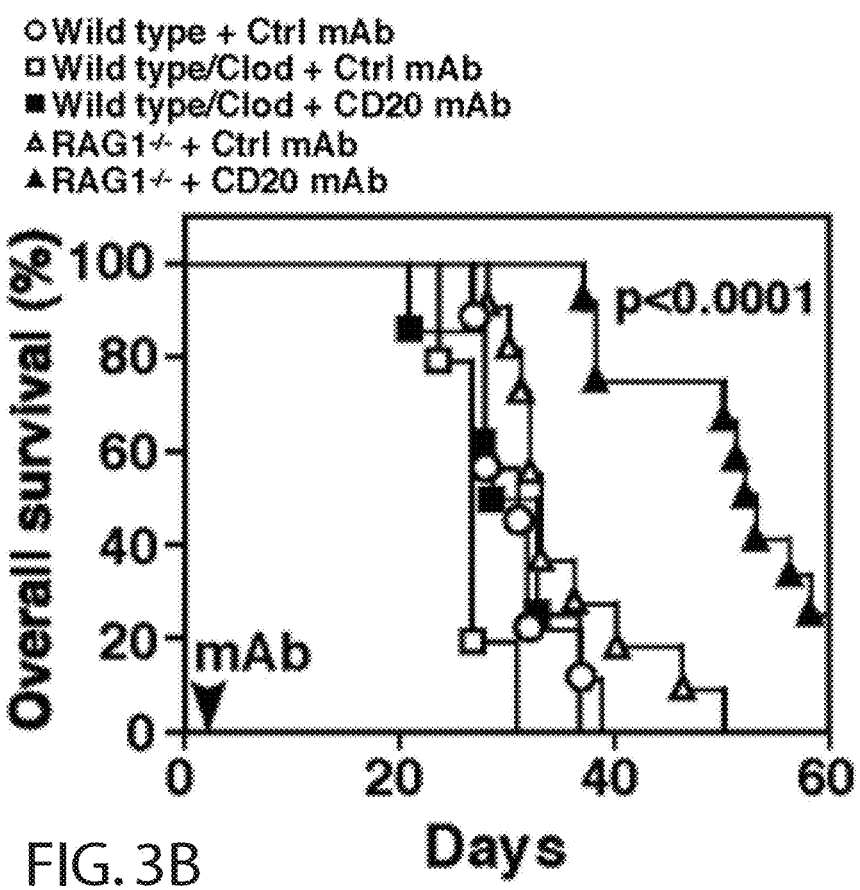
FIG. 3B shows that macrophages, but not B or T lymphocytes, mediate lymphoma depletion following CD20 mAb treatment. Wild type and Rag-1$^{-/-}$ mice (n=5-12 mice/group) were given 10$^5$ BL3750 cells on day 0 with control or CD20 mAb treatment on day 1. Some mice were treated with clodronate-encapsulated liposomes to deplete macrophages before tumor transfers as indicated.
Figure 3C:
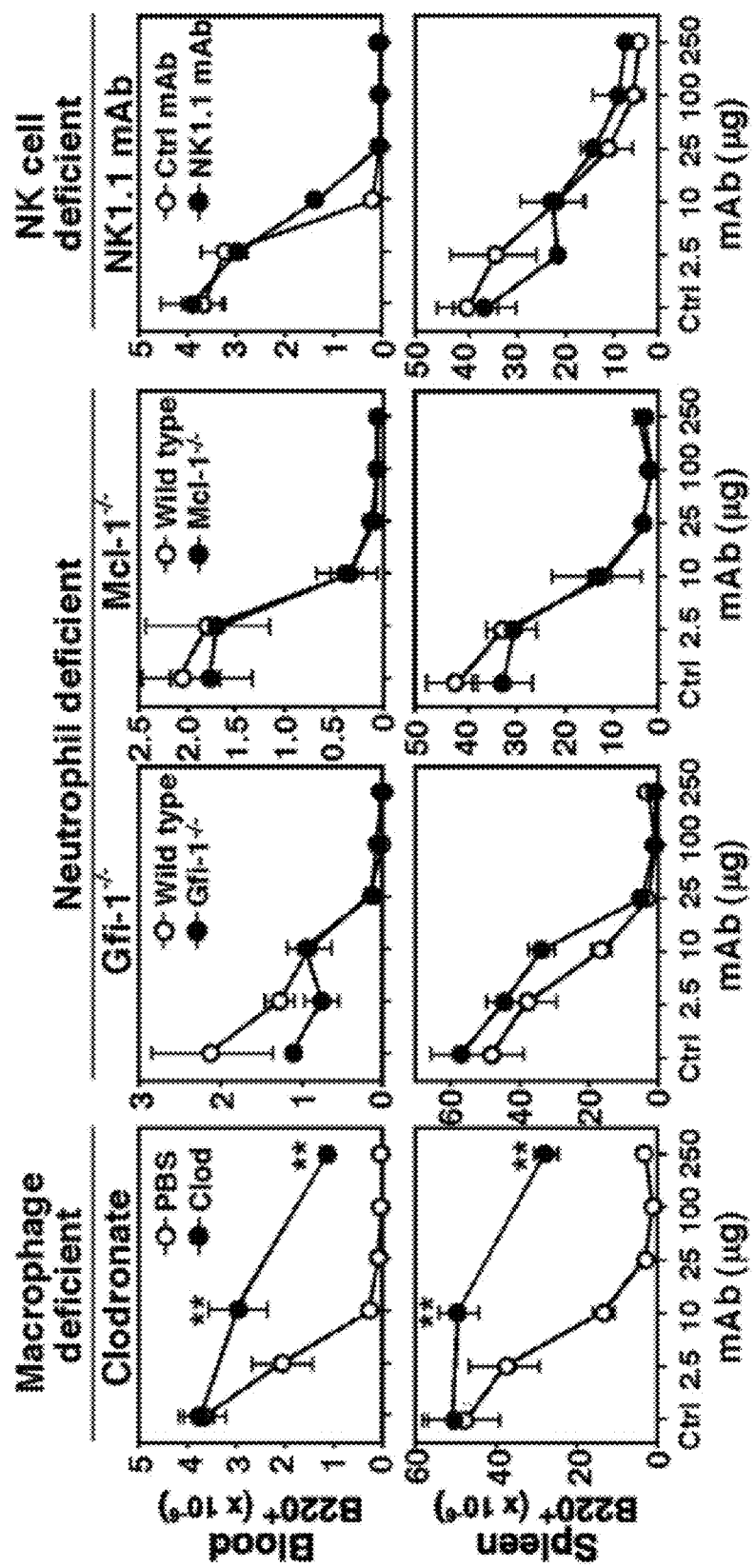
FIG. 3C shows that blood and spleen B cell numbers in macrophage- (clodronate-treated), neutrophil- (Gfi-1$^{-/-}$ or Mcl-1$^{-/-}$), or NK cell- (anti-NK1.1 mAb-treated) deficient mice (●), and their wild type littermates (○) 7 days after CD20 (2.5-250 μg) or control (250 μg) mAb treatment. Values (±SEM) represent mean B cell numbers (≥3 mice per value) at the indicated mAb doses.

CD20 immunotherapy and TLR agonist treatments. Sterile mouse anti-mouse CD20 mAb (MB20-11, IgG2c) and unreactive mouse control IgG2a mAb were as described (Minard-Colin et al., 2008). In some experiments, mice were treated with anti-NK1.1 mAb (100 g) on day −4 and day 3 for N K cell depletion. Macrophage deficiency was generated by tail vein injections of clodronate-encapsulated liposomes (Sigma-Aldrich) or control PBS-encapsulated liposomes (Van Rooijen and Sanders, 1994) 0.2 ml given on day −1 and 0.1 ml given on days 2, 5, and 9 (FIG. 3B) or 0.2 ml given on days −2, 1, and 4 (FIG. 3C). For TLR agonist treatment, mice were treated i.p. with poly I:C (150 μg; Sigma-Aldrich; InvivoGen), LPS (10 μg; Sigma-Aldrich), CpG ODN 1668 (5'tccATGACGTTCCTGAtgcT3', bases in lower case are phosphorothioate, 50 μg; Integrated DNA Technologies), or PBS concurrently with CD20 or isotype-matched control mAb. Antibodies were purified by protein A affinity chromatography (Amersham, Arlington Heights, Ill.) and determined to be endotoxin free (Limulus Amoebocyte Lysate assay, sensitivity of 0.06 EULmL, Cambrex Bio Science, Walkersville, Md.).

Cell sorting and adoptive transfer experiments. Naïve CD20$^{-/-}$ or IL-10$^{-/-}$CD20$^{-/-}$ mice were used as B cell donors. Splenic B cells were first enriched using CD19 mAb-coated microbeads (Miltenyi Biotech, Auburn, Calif.) according to the manufacturer's instructions. In addition, CD1d$^{high}$CD5 and CD1d$^{low}$CD5$^-$ B cells were isolated using a FACSVantage SE flow cytometer (Becton Dickinson) with purities of 95-98%. After purification, $2 \times 10^6$ cells were immediately transferred intravenously into C57BL/6 mice. In some experiments, B10 cell donor mice were used that had survived for 30-45 days after tumor challenge ($10^5$ BL3750 cells on day 0) and CD20 mAb treatment (250 μg on day 1). Similar results were obtained when the donor B cells were isolated from naïve mice or mice that has survived BL3750 challenge so all results were pooled.

TLR transcript expression. Total RNA from whole spleen cells, splenic B cells purified using B220-mAb coated microbeads, and BL3750 cells was isolated using TRIzol reagent (Invitrogen, Carlsbad, Calif.). Random hexamer primers (Promega, Madison, Wis.) and Superscript II RNase H Reverse Transcriptase (Invitrogen) were used to generate cDNA. PCR primer pairs were used to amplify TLR transcripts as described (Edwards et al., 2003). In addition, relative TLR transcripts were quantified by GeneChip analysis (Affymetrix Mouse Genome 430 2.0 GeneChips; Affymetrix, Santa Clara, Calif.). Transcript levels were normalized per chip to the 50$^{th}$ percentile. All quality parameters for the arrays were confirmed to be in the range recommended by the manufacturer.

Proliferation assay. Splenic B cells were purified using CD19 mAb-coated microbeads (Miltenyi) and labeled with CFSE Vybrant™ CFDA SE fluorescent dye (5 μM; Invitrogen). Labeled B cells were then cultured in medium with LPS, CpG, or poly I:C (25 μg/ml) for 72 h and assessed by flow cytometry.

Cytokine ELISA. Secreted IL-10 was quantified by ELISA. Purified B cells ($4 \times 10^5$) were cultured in 0.2 ml of complete medium with TLR agoninsts (25 μg/ml) in a 96-well flat-bottom tissue culture plates. Culture supernatant fluid IL-10 concentrations were quantified using IL-10 OptEIA ELISA kits (BD PharMingen) bfollowing the manufacturer's protocols. All assays were carried out using triplicate samples.

Nitric oxide production. To measure nitric oxide (NO) production, nitrite formed by the spontaneous oxidation of NO was measured. Culture supernatant fluid nitrite concentrations were quantified using Griess Reagent Kit (Invitrogen-Molecular Probes) following the manufacturer's protocols. All assays were carried out using duplicate samples.

In vitro assay of antibody-dependent phagocytosis. Spleen B cells were purified by MACS B cell isolation (Miltenyi Biotech), labeled with CFSE Vybrant™ CFDA SE fluorescent dye (5 µM; Invitrogen) and cultured over night in complete medium. CFSE-labeled B cells were incubated with CD20 mAb (MB20-11) on ice for 1 h, and washed with complete medium to remove unbound mAb. Macrophages were isolated from the peritoneal cavity of thioglycolate-treated mice by lavage. Peritineal macrophages were further purified by adherence to plastic before culture with or without poly I:C (25 µg/ml) in complete medium at 37° C. in a 5% $CO_2$ atmosphere for 18 h. Macrophages and B cells were mixed at a 1:1 ratio and cultured for 2.5 h. The cell mixture was then stained with PE-conjugated CD11b mAb with the percentage of $CFSE^+CD11b^+$ (double-positive cells) analyzed by flow cytometry.

Statistical analysis. Statistical comparisons of differences between sample means used the Student's t test. The generation of Kaplan-Meier cumulative survival plots and Log-Rank test comparisons of survival used Prism software (version 4.0; GraphPad Software. San Diego, Calif.). Spearman's rank correlation coefficient was used to examine the relationship between 2 variables.

Results

Endogenous B Cells Inhibit Lymphoma Immunotherapy

Figure 1B:
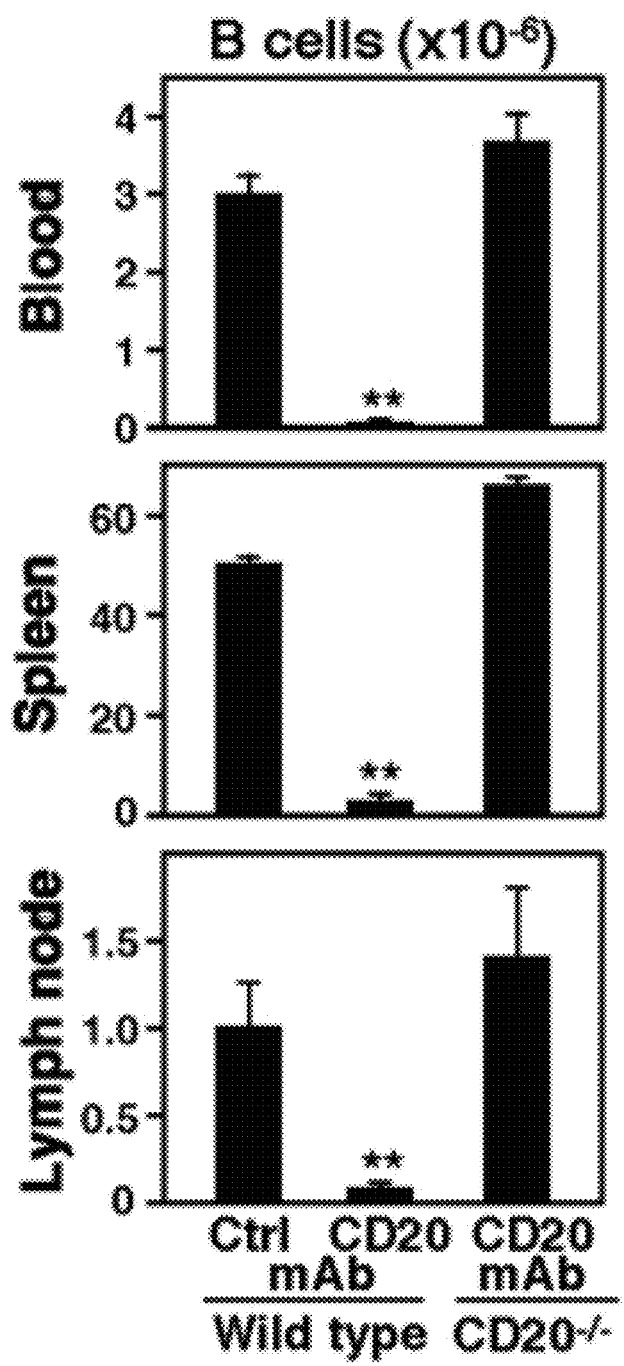
FIG. 1B shows $B220^+$ B cell numbers in wild type and $CD20^{-/-}$ mouse tissues 7 days after control or CD20 mAb treatment. Blood numbers represent cells $\times 10^{-6}$/ml. Values represent means (±SEM) for 3 mice in each group.
Figure 1C:
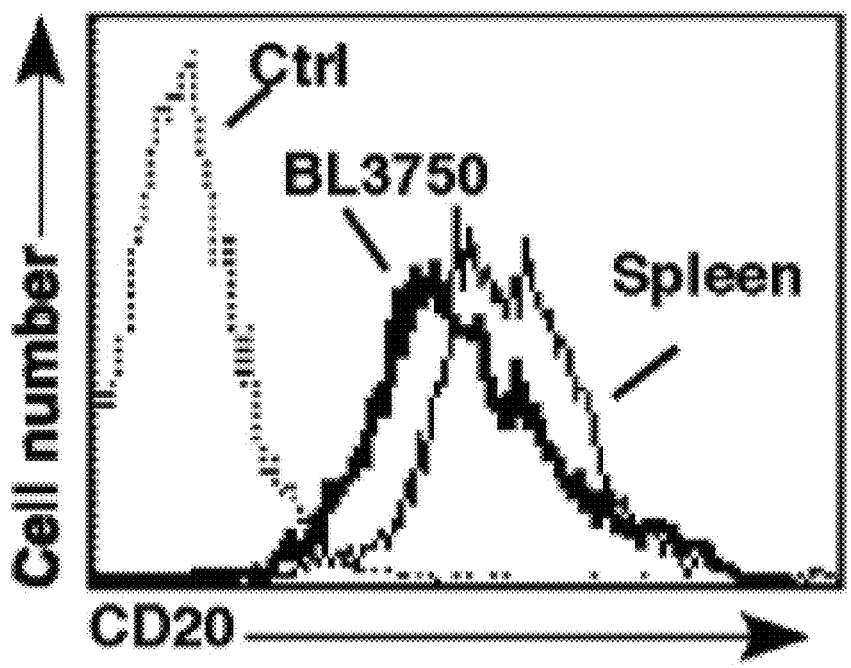
FIG. 1C shows CD20 expression by BL3750 lymphoma cells. BL3750 cells (thick line) and spleen $B220^+$ cells from $E\mu$-cMycTG$^{+/-}$ mice (thin line) were assessed by three-color immunofluorescence staining with flow cytometry analysis. Background staining using a control (Ctrl) mAb is shown (dotted line). Results are representative of two independent experiments.
Figure 1D:
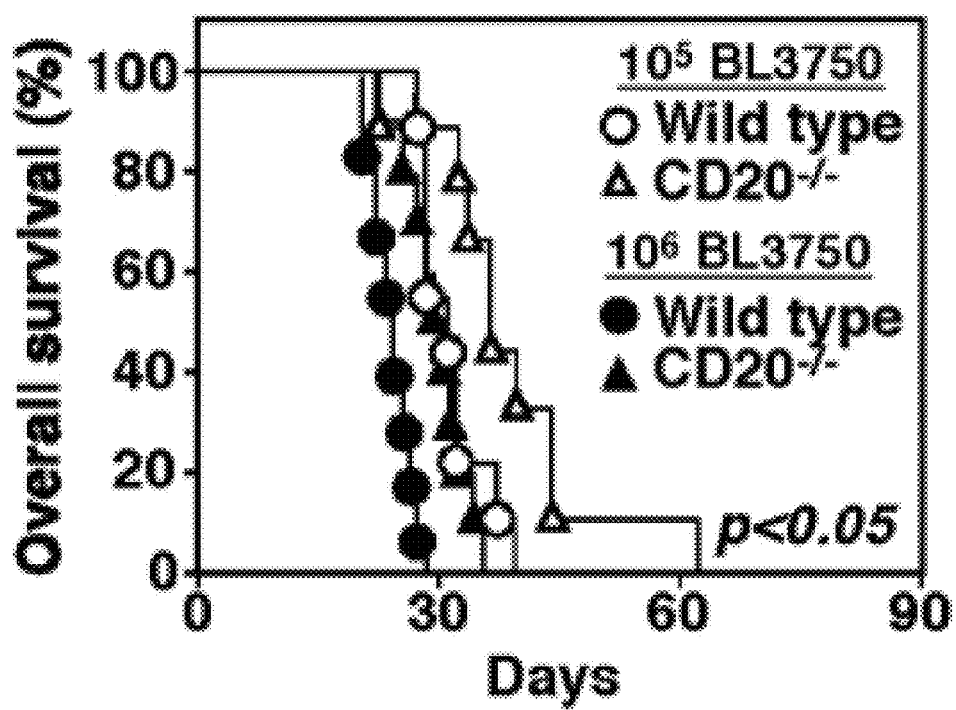
FIG. 1D shows survival of wild type and $CD20^{-/-}$ mice given $10^5$ or $10^6$ BL3750 cells on day 0 with n=9-18 mice in each group.
Figure 1E:
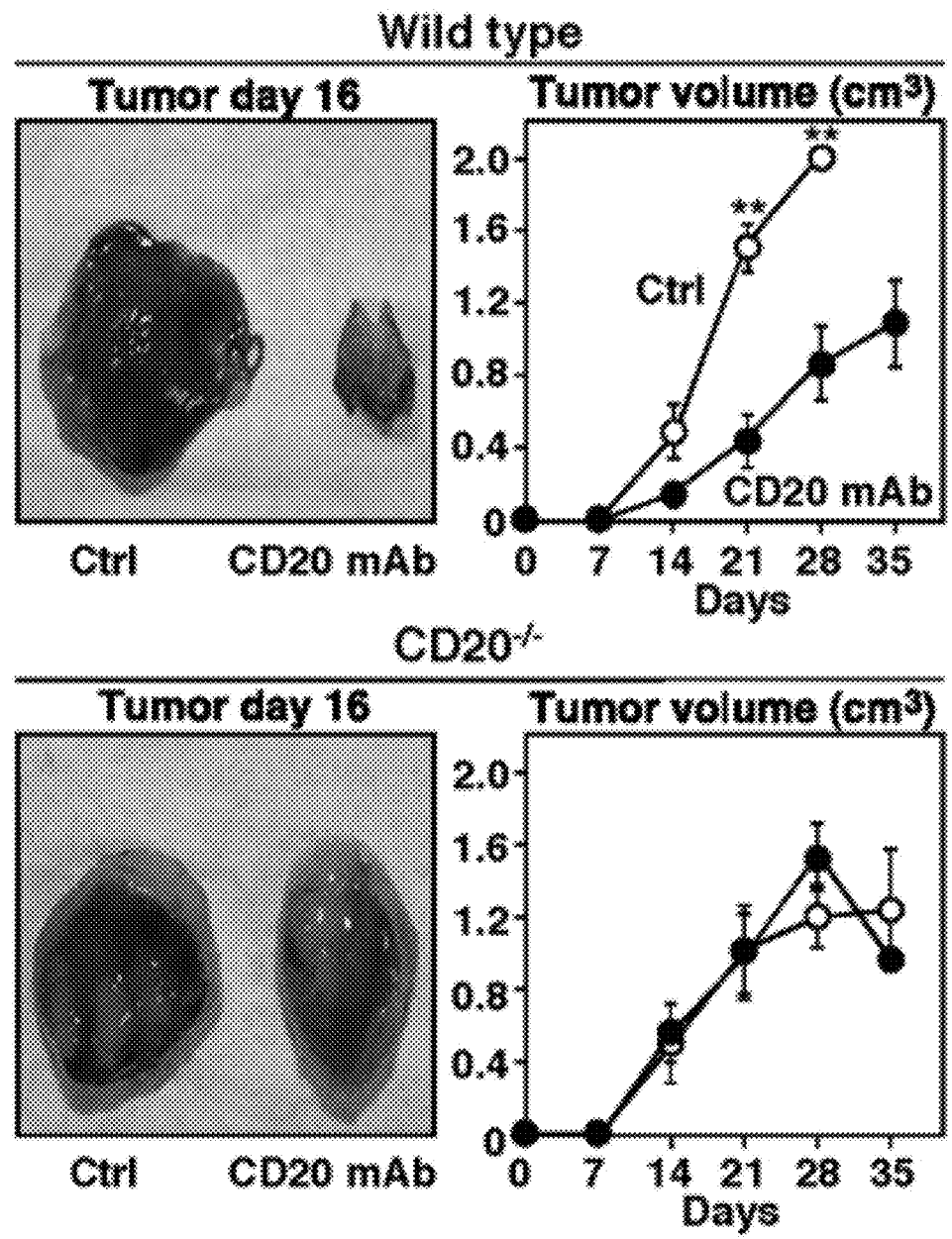
FIG. 1E shows Representative dorsal tumors resected from control or CD20 mAb-treated wild type mice or $CD20^{-/-}$ mice 16 days after receiving $10^6$ BL3750 cells. Line graphs indicate tumor volumes (±SEM) for wild type or $CD20^{-/-}$ mice given CD20 (●) or control (○) mAb on days 1 and 7 following the transfer of $10^6$ BL3750 cells. Values represent mean (±SEM) tumor volumes observed in 3-6 mice for each group from 2 independent experiments.
Figure 1F:
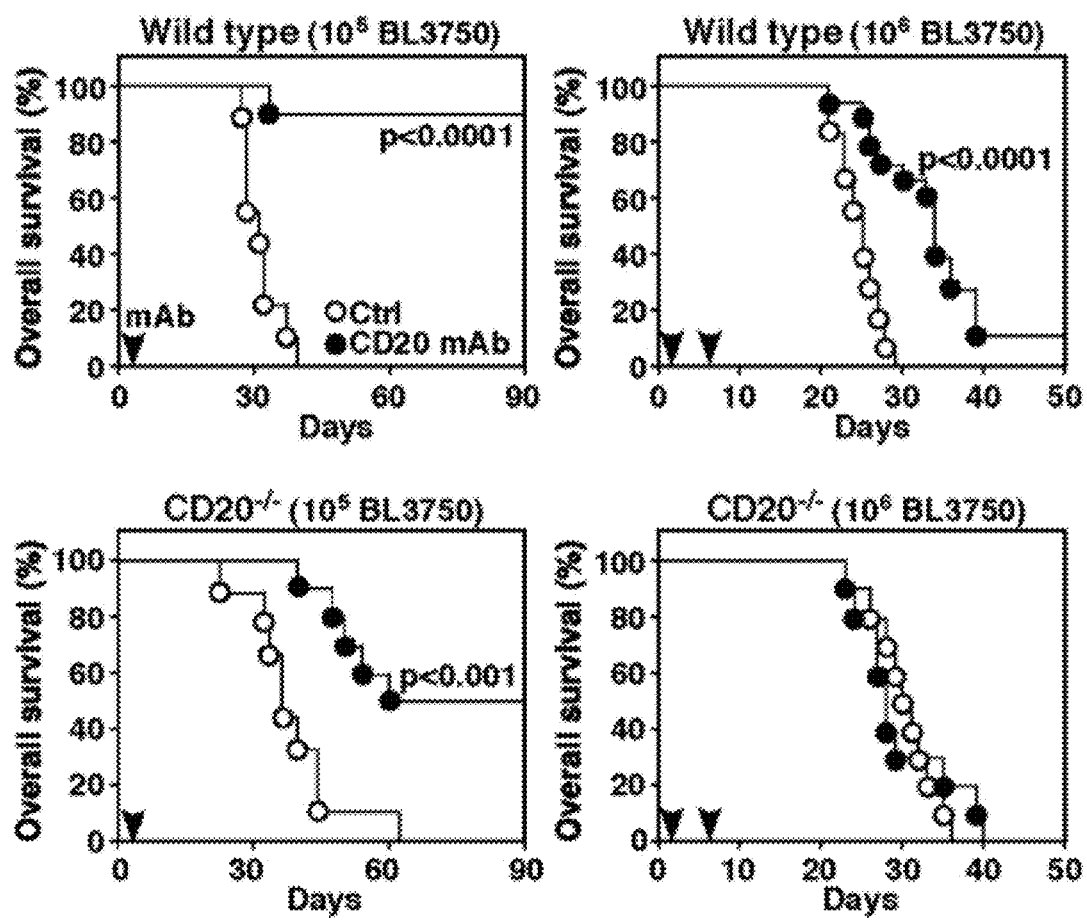
FIG. 1F shows survival of wild type or $CD20^{-/-}$ mice given $10^5$ (n=9-10 mice/group; left panels) or $10^6$ (n=10-18 mice/group; right panels) BL3750 cells on day 0 with CD20 (●) or control (○) mAb given on day 1 or days 1 and 7 (arrowheads) in ≥3 independent experiments.
Figure 1G:
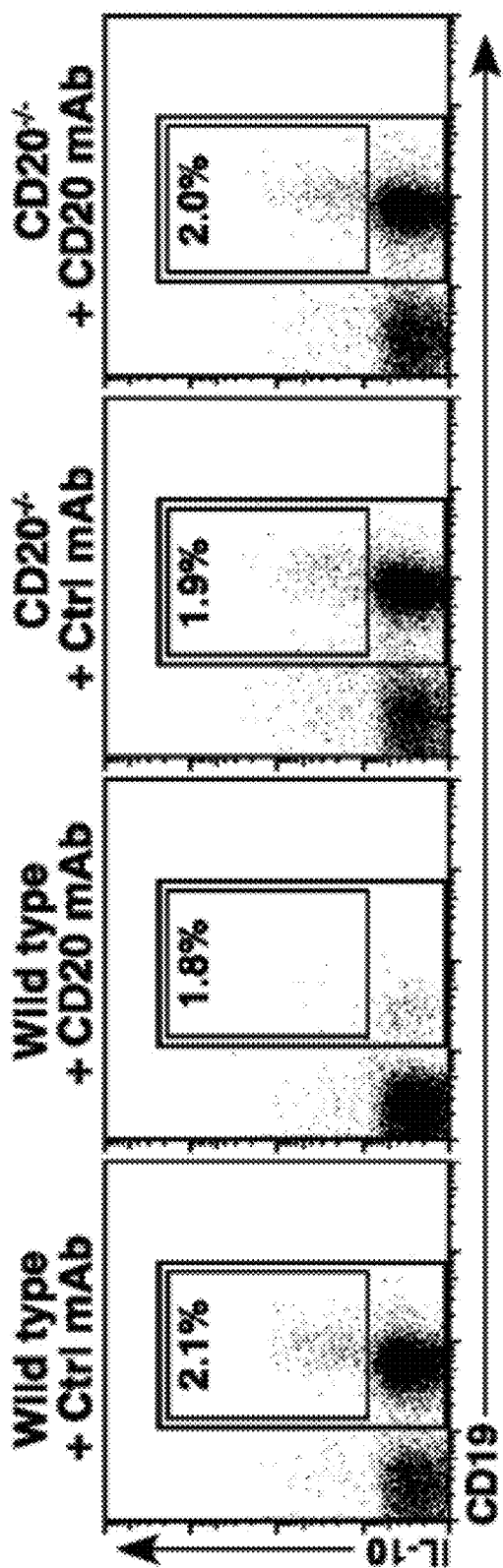
FIG. 1G shows representative frequencies of IL-10 producing B cells among spleen $CD19^+$ B cells in control or CD20 mAb-treated wild type or $CD20^{-/-}$ mice. The bar graph represents IL-10 producing B cell numbers 7 days after control or CD20 mAb treatment. Values represent mean (±SEM) observed in ≥3 mice per value from 2 independent experiments.

A single dose of mouse anti-mouse CD20 mAb (MB20-11) but not control mAb (250 µg/mouse) depletes >95% of mature B cells in all lymphoid tissues after 7 days in wild type mice (FIG. 1A-B), with the effect lasting up to 8 weeks (Minard-Colin et al., 2008; Uchida et al., 2004a). The role of B cells during lymphoma immunotherapy was examined using $CD20^+$ Burkitt's-like lymphoma cells (BL3750, FIG. 1C) that were maintained as frozen stocks of primary cell cultures (Minard-Colin et al., 2008). Wild type mice given $10^5$ BL3750 cells on day 0 developed detectable tumors at the site of injection by 12-19 days, with a median survival of 31 days (range 27-39, FIG. 1D). This is a standard mouse model of human lymphoma and is used by those skilled in the art. CD20 mAb given 1 day after BL3750 cell transfer depleted normal B cells and had a significant therapeutic effect on tumor growth, with 89% of mice remaining disease free for ≥60 days (p<0.0001. FIG. 1F). Transplantation of $10^6$ BL3750 cells resulted in death of all control mAb-treated mice (median 25 days, range 21-29), with CD20 mAb treatment on days 1 and 7 delaying tumor growth and extending median survival to 34 days (p<0.0001, FIG. 1E-F). Thereby, BL3750 cells provide a syngeneic mouse lymphoma model for mechanistic studies that can be used for quantifying the response of Burkitt's-like lymphoma cells to CD20 immunotherapy in vivo.

In comparison with wild type littermates, CD20 mAb did not deplete B cells in $CD20^{-/-}$ mice (FIG. 1A-B), even though their B cell and immune system development are normal (Uchida et al., 2004b). $CD20^{-/-}$ mice given $10^5$ BL3750 cells on day 0 developed detectable tumors by 14-25 days, with a median survival of 36 days (range 22-62, FIG. 1D). Prolonged survival in $CD20^{-/-}$ mice relative to wild type littermates given BL3750 cells is likely to result from immune responses generated against CD20 present on lymphoma cells as previously demonstrated (Uchida et al., 2004b). Regardless, CD20 mAb treatment resulted in only 50% of $CD20^{-/-}$ mice remaining disease free for up to 60 days when given $10^5$ $CD20^+$ BL3750 cells (p<0.001; FIG. 1E-F). Tumor growth and survival were equivalent in $CD20^{-/-}$ mice given $10^6$ BL3750 cells regardless of CD20 (median 28 days, range 23-40) or control (median 31 days, range 23-36) mAb treatment. Thus, the persistence of endogenous B cells in $CD20^{-/-}$ mice significantly inhibited the anti-tumor effects of CD20 mAb that were observed in wild type mice.

B10 Cells Inhibit CD20 Immunotherapy

Figure 2A:
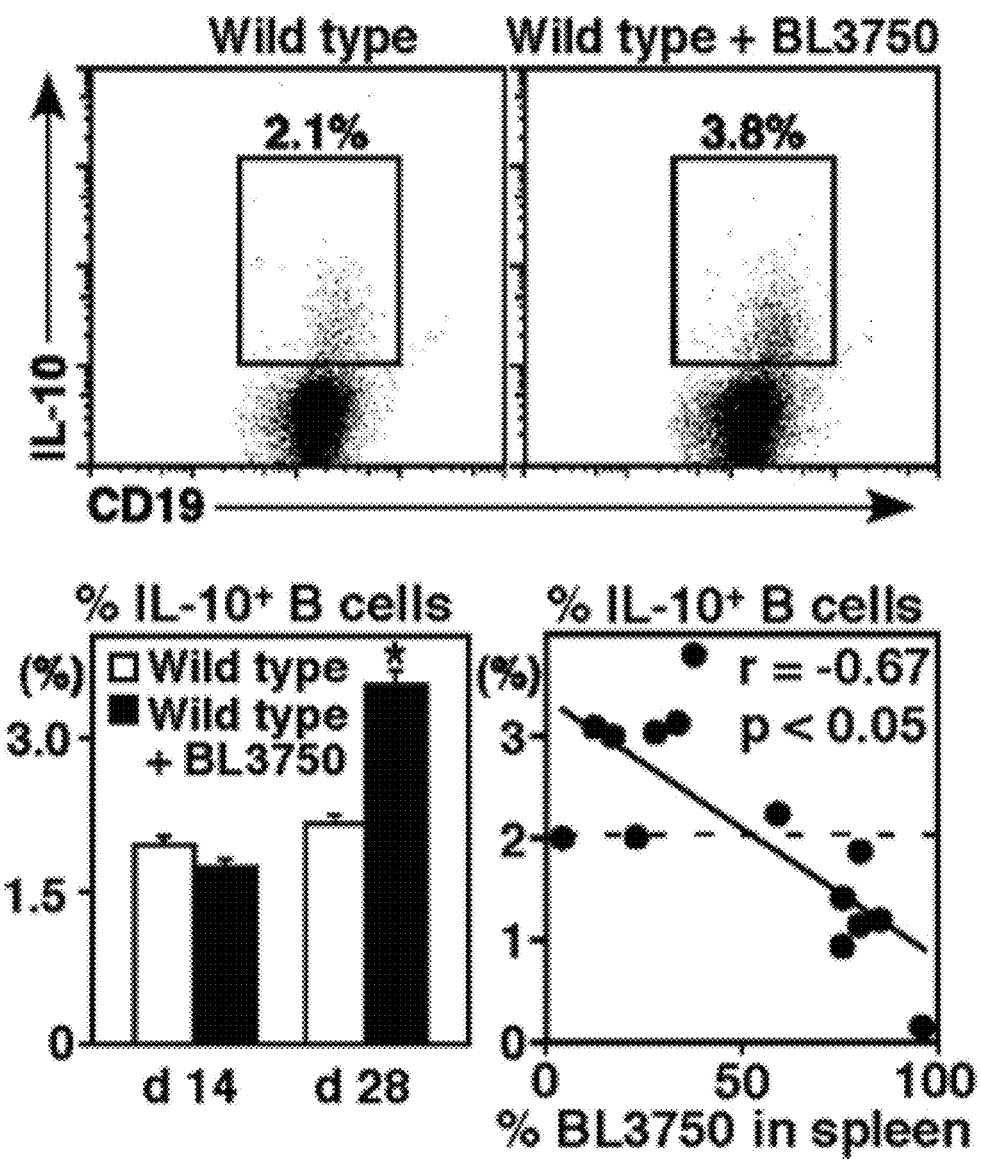
FIG. 2A shows spleen B10 cell frequencies increase during lymphoma progression. Representative dot plot histograms showing $IL-10^+$ B cell frequencies in an untreated mouse or littermate 28 days after BL3750 cell transfer (top panels). Bar graphs indicate mean (±SEM) percentages of B cells that produced IL-10 (n=3 mice/group). Scatter plots compare frequencies of IL-10 producing CD19+ non-malignant B cells with lymphoma invasion (% of BL3750 cells among total leukocytes) from individual mice 21-35 days following BL3750 cell transfers. The dashed line indicates the mean percentage of IL-10+ B cells in mice without tumors.

Since IL-10-competent B10 cells regulate inflammation and immune responses, their role in CD20 immunotherapy was evaluated. B10 cells were identified by their ability to express cytoplasmic IL-10 after appropriate stimulation and their $CD1d^{high}CD5^+$ phenotype (Yanaba et al., 2009). Negative controls for IL-10 staining included isotype-matched control mAb and B cells from IL-10-deficient ($IL-10^{-/-}$) mice. Spleen B10 cell frequencies and numbers were equivalent in wild type and $CD20^{-/-}$ mice (FIG. 10). CD20 mAb treatment depleted all B10 cells from wild type mice, but not from $CD20^{-/-}$ mice. Remarkably, B10 cell frequencies also expanded 2-fold in tumor-bearing wild type (FIG. 2A) and $CD20^{-/-}$ mice (data not shown) by day 28. However, the relative frequency of spleen B10 cells decreased significantly as BL3750 cells displaced spleen lymphocytes, which argues that B10 cells were not required for lymphoma progression.

Figure 2B:
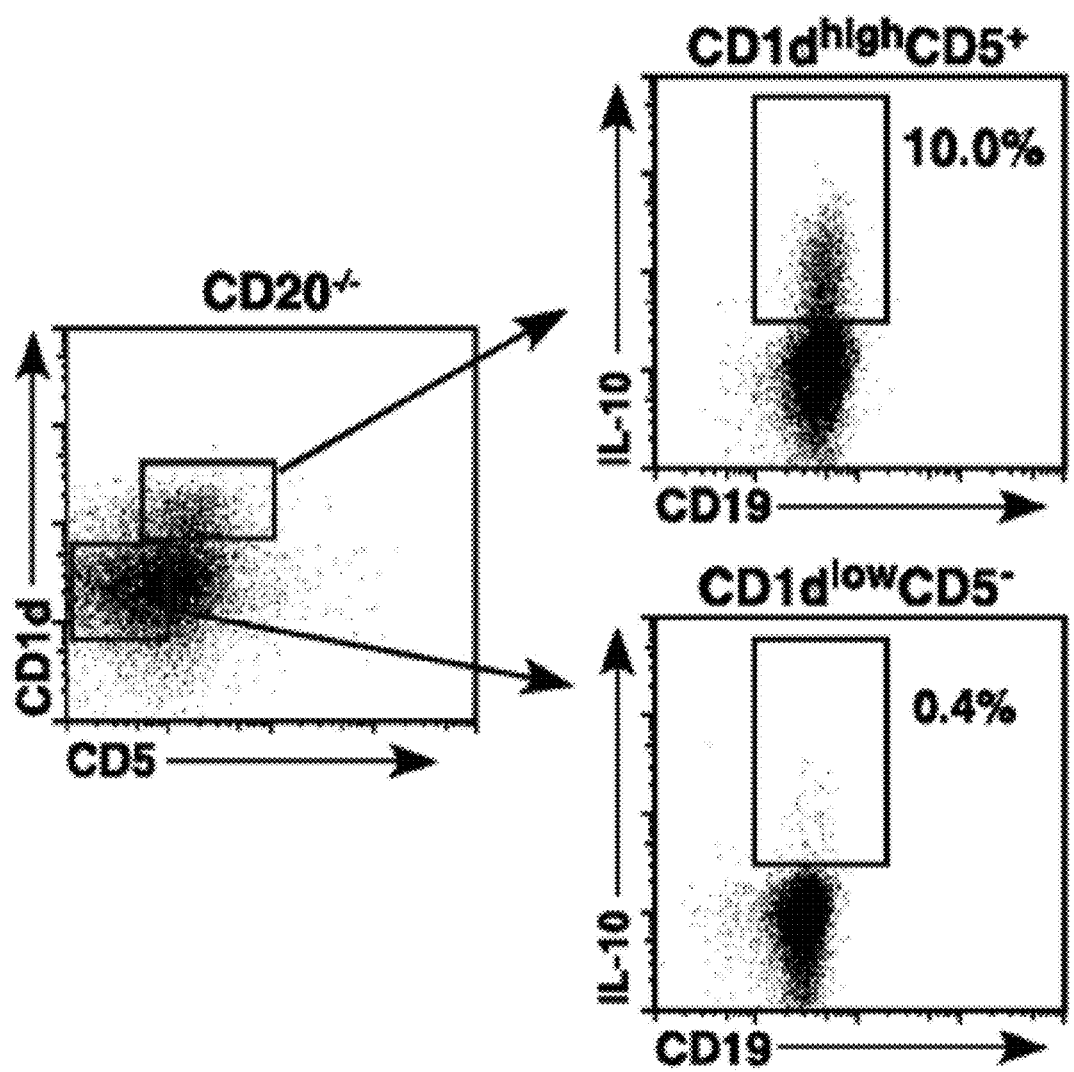
FIG. 2B shows representative purification of splenic CD1d$^{high}$CD5+CD19+ and non-CD1d$^{high}$CD5+CD19+ B cell subsets from CD20$^{-/-}$ mice. The frequency of IL-10 competent B10 cells within each subset is shown. Percentages indicate mean IL-10+ B cell frequencies as determined by flow cytometry analysis in 4 independent experiments.
Figure 2C:
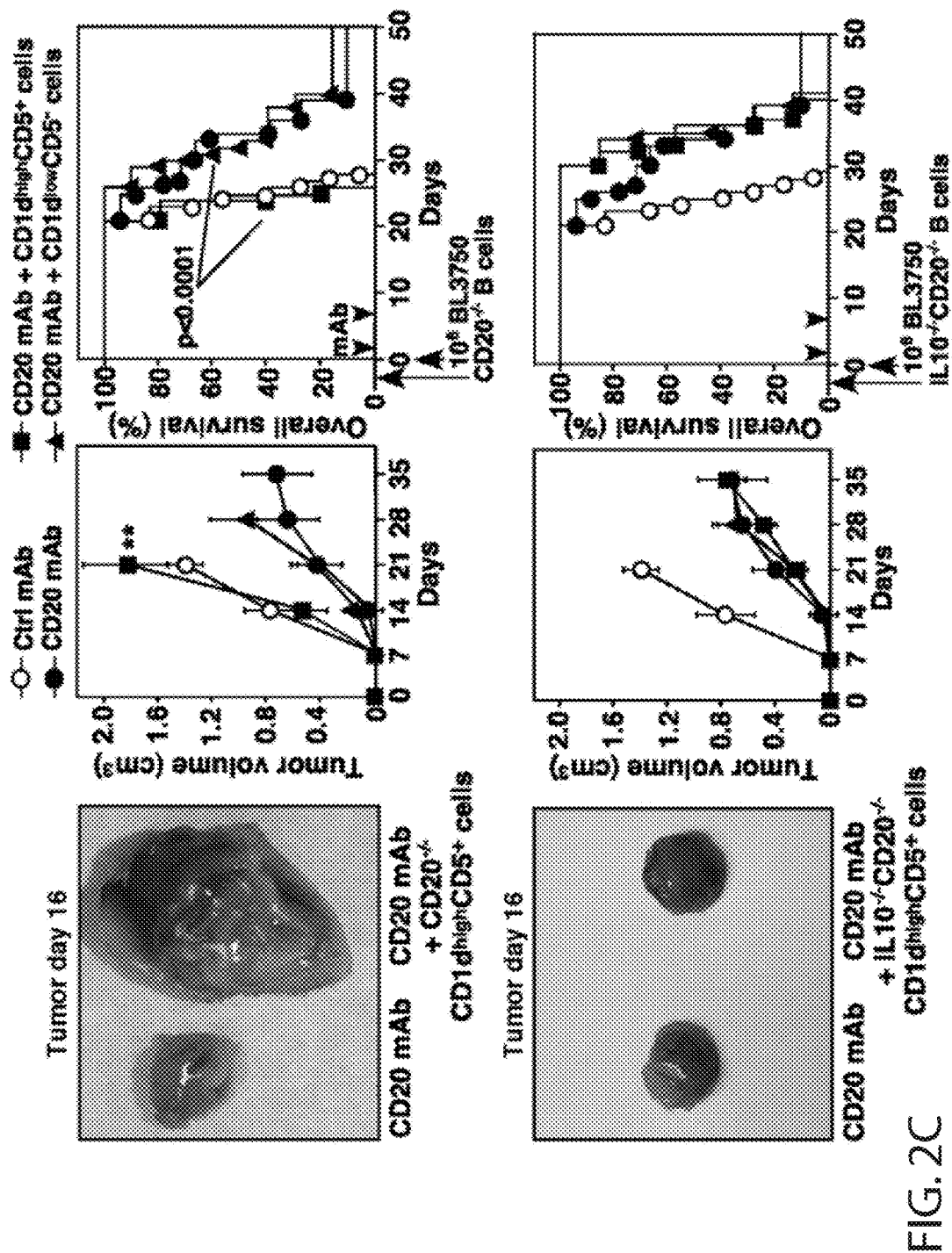
FIG. 2C shows CD1d$^{high}$CD5+ B cells inhibit lymphoma depletion by CD20 mAb through IL-10 production. B cell subsets purified from CD20$^{-/-}$ or IL-10$^{-/-CD}$20$^{-/-}$ mice were given to wild type recipients (2×10$^6$/mouse) one day before receiving 10$^6$ BL3750 tumor cells on day 0. CD20 or control mAbs (arrowheads) were given on days 1 and 7. Representative dorsal tumors were resected from mice on day 16. Tumor volumes (±SEM) and overall mouse survival were quantified after tumor challenge and control (○), CD20 mAb (●), CD20 mAb plus CD1d$^{high}$CD5+ B cell (■), or CD20 mAb plus non-CD1d$^{high}$CD5+ B cell (▲) treatments (n=10-18 mice/group). Results represent pooled data from 4 independent experiments.

To determine whether B10 cells inhibited the anti-tumor effects of CD20 mAb in vivo, $CD1d^{high}CD5^+$ B cells or conventional non-$CD1d^{high}CD5^+$ B cells were purified from $CD20^{-/-}$ mice (FIG. 2B) and adoptively transferred into wild type mice. B10 cells represented 9-11% of the spleen $CD1d^{high}CD5^+$ B cell subset (FIG. 2B). Thereby, the adoptive transfer of $2 \times 10^6$ $CD1d^{high}CD5^+$ B cells included ~$2 \times 10^5$ IL-10-competent B10 cells, while B10 cells represented <1% of non-$CD1d^{high}CD5^+$ B cells. Recipient mice were given $10^6$ BL3750 cells one day later (day 0), followed by CD20 or control mAb treatment. CD20 mAb treatment of wild type mice delayed tumor growth and prolonged survival (median 34 days, range 21-39; p<0.0011; FIG. 2C). The adoptive transfer of $CD20^{-/-}CD1d^{low}CD5^-$ B cells was without effect. By contrast, the adoptive transfer of $CD20^{-/-}$ $CC1d^{high}CD5^+$ B cells eliminated the therapeutic benefit of CD20 mAb treatment, and reduced survival to levels observed in control mAb treated mice (median 24 days, range 21-26).

Whether B10 cell IL-10 production was responsible for eliminating the therapeutic benefit of CD20 mAb treatment was determined using $CD1d^{high}CD5^+$ and non-$CD1d^{high}CD5^+$ B cells from $IL-10^{-/-}CD20^{-/-}$ mice transferred into wild type mice given CD20 mAb. The adoptive transfer of either $CD1d^{high}CD5^+$ or $CD1d^{low}CD5^-$ B cells from $IL-10^{-/-}CD20^{-/-}$ mice did not affect tumor growth or mouse survival following CD20 mAb treatment (FIG. 2C). IL-10 competent B10 cells develop normally in $IL-10^{-/-}$ mice as equal numbers of $CD1d^{high}CD5^+$ B cells from wild type and $IL-10^{-/-}$ mice express an independent IL-10 reporter gene following stimulation. Furthermore, IL-10 production by B10 cells was unlikely to influence BL3750 growth since lymphoma progression was identical in wild type and $IL-10^{-/-}$ mice (FIG. 3A). Thereby, B10 cells negatively regulated CD20 mAb-induced lymphoma depletion through the production of IL-10.

B10 Cells Regulate Macrophage Activation

To determine how B10 cells regulate CD20 mAb-induced lymphoma depletion, the relative contributions of innate effector cells to lymphoma and B cell depletion by CD20 mAb was assessed. CD20 mAbs deplete normal and malignant B cells through IgG Fc receptors (FcγR) (Minard-Colin et al., 2008), which are predominantly expressed by macrophages, neutrophils, NK cells, and dendritic cells. Lymphoma depletion was dependent on monocytes as their clodronate-induced depletion from tumor-bearing mice (Wild type/Clod) eliminated the therapeutic benefit of CD20 mAb (FIG. 3B) as described (Minard-Colin et al., 2008). Likewise, macrophage depletion significantly reduced blood and spleen B cell clearance over a range of CD20 mAb concentrations (FIG. 3C). Lymphoma depletion did not require endogenous B or T cells as CD20 mAb treatment significantly prolonged the survival of Rag-1$^{-/-}$ mice given BL3750 cells (FIG. 3B). B cell depletion was also compared in neutrophil-deficient Mcl-1$^{-/-}$ or Gfi-1$^{-/-}$ mice, and in mice depleted of NK cells by NK1.1 mAb. Mcl-1$^{-/-}$ mice have 80-86% reductions in blood and spleen neutrophils, but have normal macrophages (Dzhagalov et al., 2007). Gfi-1$^{-/-}$ mice lack phenotypically mature neutrophils, while morphologically normal monocytes are present in normal numbers (Hock et al., 2003). Splenic B220$^+$ B cells from wild type, Mcl-1$^{-/-}$, and Gifi-1$^{-/-}$ mice expressed cell surface CD20 at identical levels (data not shown). NK1.1 mAb-treatment reduced circulating NK cells by 93±2% as determined by DX5 mAb staining (data not shown). However, CD20 mAb treatment depleted similar numbers of blood or spleen B cells in Mcl-1$^{-/-}$, Gfi-1$^{-/-}$, and NK cell-depleted mice and their wild type littermates after 7 days. Thus, CD20 mAb-induced lymphoma and B cell depletion was predominantly macrophage dependent.

Figure 3D:
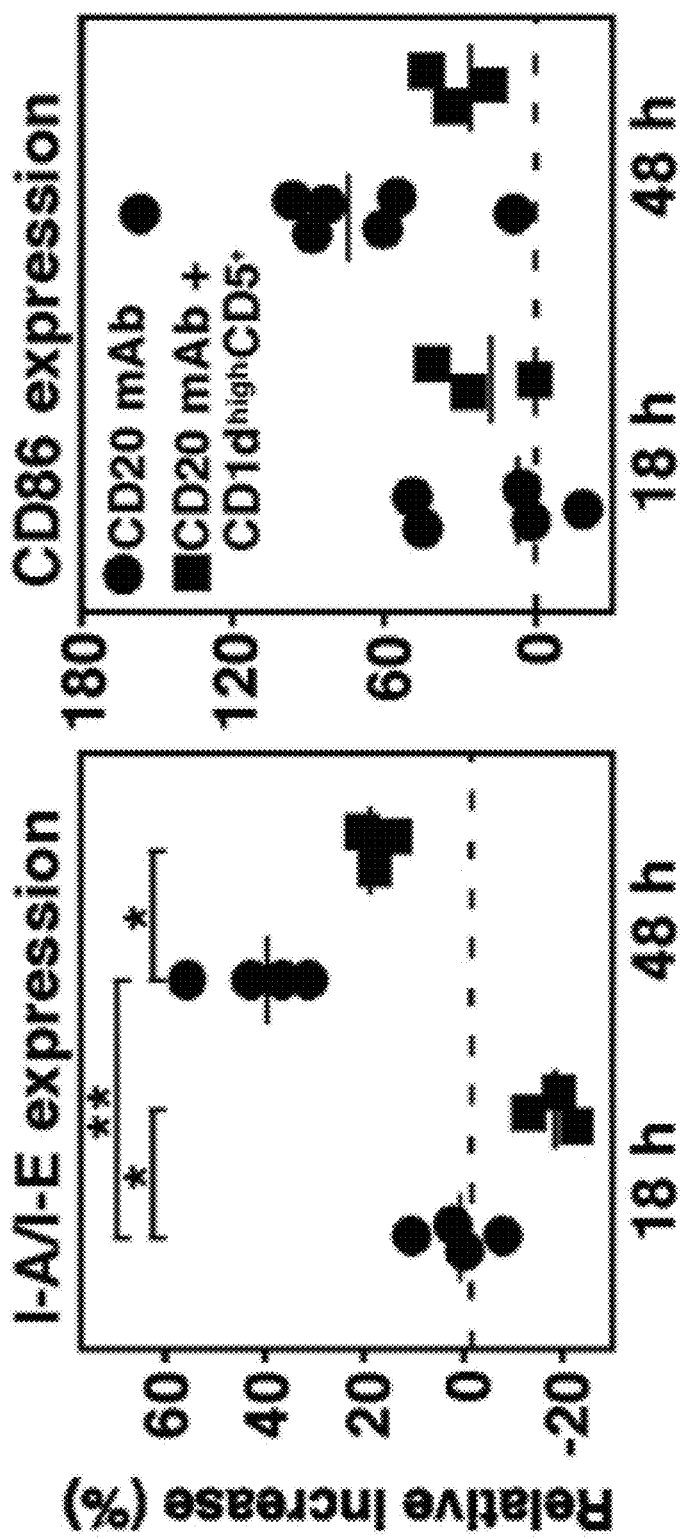
FIG. 3D shows that CD1d$^{high}$CD5+ B cells inhibit macrophage activation in vivo. Wild type mice were untreated (●) or given CD1d$^{high}$CD5+ B cells from CD20$^{-/-}$ mice (■, 2×10$^6$/mouse) one day before BL3750 cell transfer followed by CD20 mAb treatment. Spleen cells were harvested 18 and 48 h after CD20 mAb treatment, with CD11b+ F4/80+I-A/I-E+ cells assessed for MHC class II (I-A/I-E) expression and CD11b+F4/80+ cells for CD86 expression by immunofluorescence staining. Graphs indicate an increase (%) in mean fluorescence staining intensities relative to wild type mice treated with control mAb (dashed horizontal lines). Values represent individual mice, with horizontal bars indicating means. Significant differences between means are indicated; *p<0.05, **p<0.01.
Figure 3E:
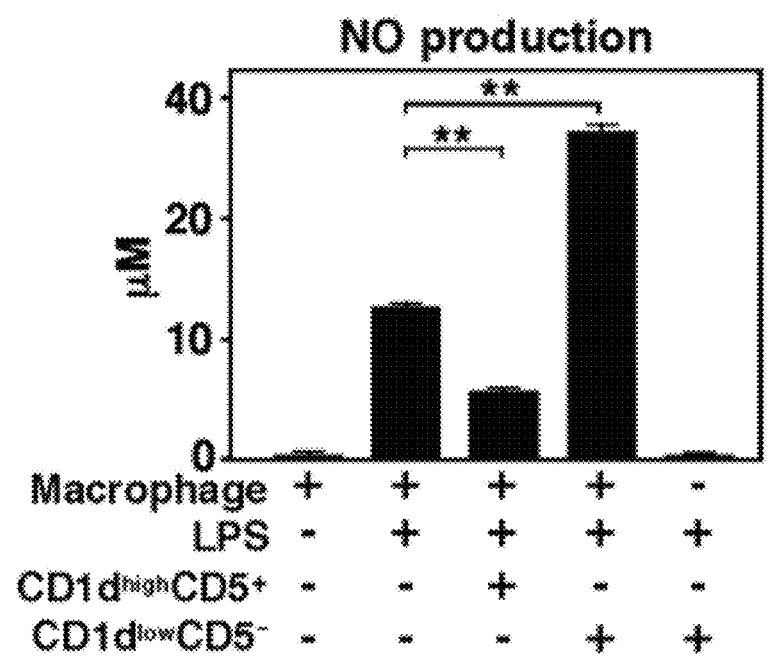
FIG. 3E shows that CD1d$^{high}$CD5+ B cells inhibit macrophage nitric oxide production in vitro. Purified splenic CD1d$^{hi}$CD5+ or CD1d$^{lo}$CD5$^-$ B cells were stimulated with LPS (10 μg/ml) overnight. CD11b+ bone marrow cells were cultured with LPS-primed CD1d$^{high}$CD5+ or CD1d$^{low}$CD5+ B cells for 48 h, with LPS (1 μg/m) added during the final 18 h of culture. Values represent mean (±SEM) culture supernatant fluid nitrite concentrations from 2 independent experiments.

Since monocytes express IL-10 receptor at high-levels (Moore et al., 2001), the effect of adoptively transferred B10 cells on monocyte activation was examined in viva. Spleen CD1d$^{high}$CD5$^+$ B cells were purified from CD20$^{-/-}$ mice and transferred into wild type mice that were given BL3750 cells followed by CD20 mAb one day later. Forty-eight hours after CD20 mAb treatment, activation-induced upregulation of major histocompatability class II molecule was significantly reduced in mice given CD1d$^{high}$CD5$^+$ CD20$^{-/-}$ B cells (FIG. 3D). Activation-induced CD86 expression was also reduced in mice given CD1d$^{high}$CD5$^+$ CD20$^{-/-}$ B cells. LPS-induced nitric oxide production was also significantly reduced when macrophages were co-cultured with CD1d$^{high}$CD5$^+$ B cells, but was significantly increased when macrophages were co-cultured with CD1d$^{low}$CD5$^-$ B cells (FIG. 3E). Thus, CD1d$^{hi}$CD5$^+$ B cells can significantly reduce monocyte activation and thereby negatively regulate CD20 mAb efficacy in vivo.

TLR Activation Enhances CD20 mAb Efficacy In Vivo

Figure 4A:
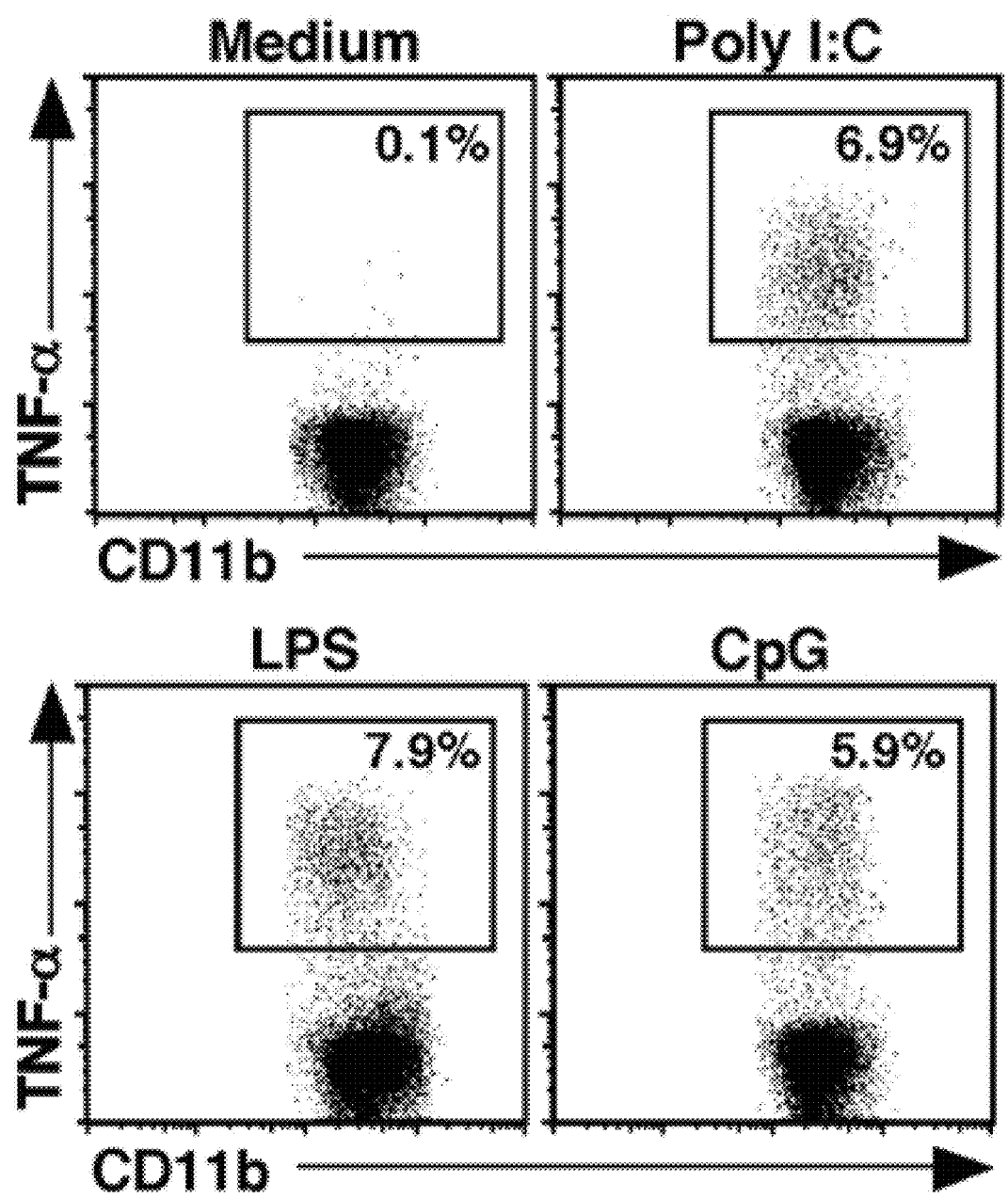
FIG. 4A shows representative TLR-induced TNF-α production by CD11b+ bone marrow cells cultured for 4 h in medium containing Brefeldin A. Percentages indicate relative frequencies of cells within the gates shown.
Figure 4B:
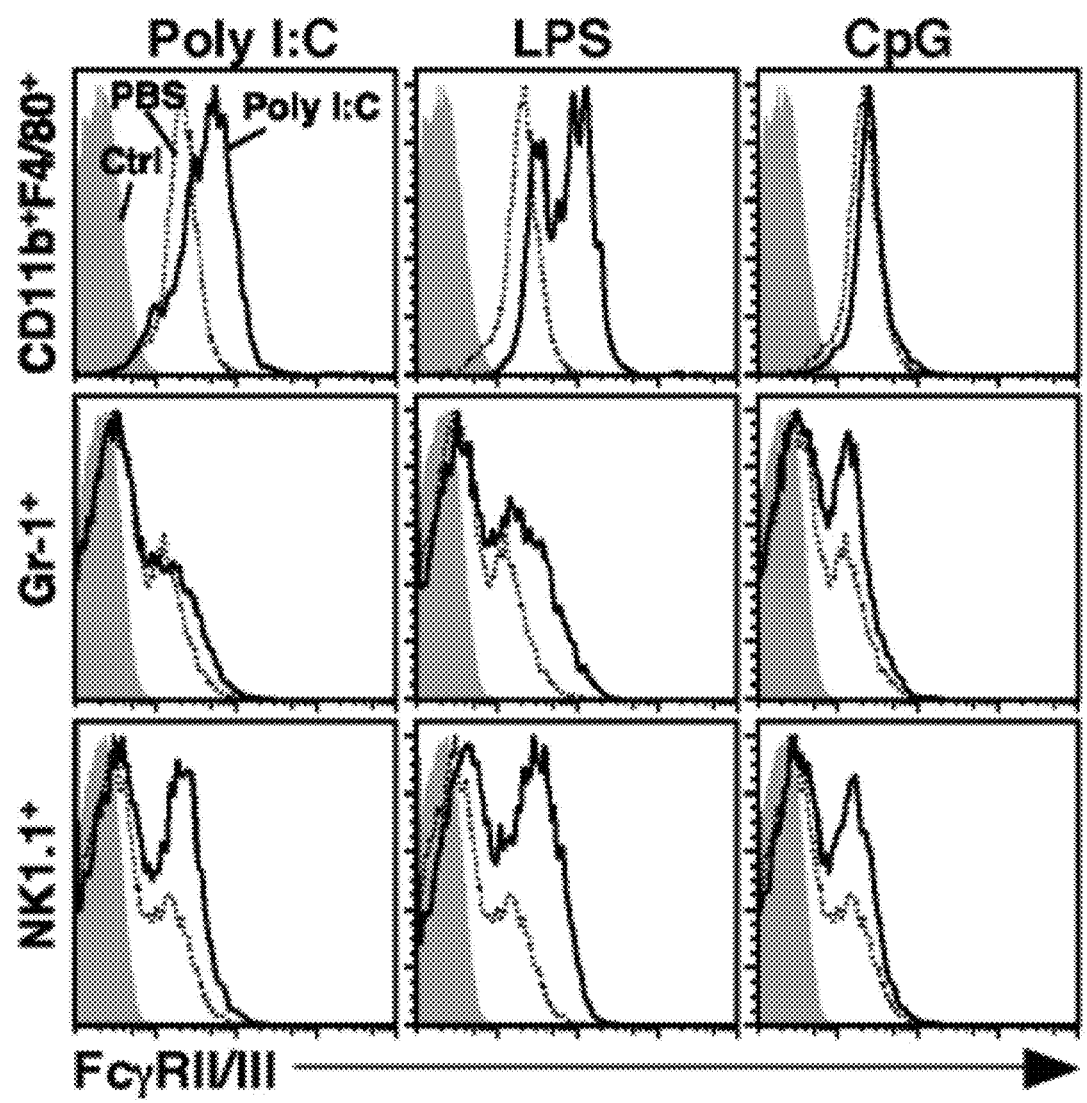
FIG. 4B shows representative FcγR expression by spleen CD11b+F4/80+ macrophages, Gr-1+ neutrophils, and NK1.1+ NK cells following control PBS or TLR agonist treatment. Splenocytes were isolated from mice 18 h later and analyzed for FcγRII/III expression by immunofluorescence staining. For FIGS. 4A-B the results represent 2 independent experiments.

The results shown herein that B10 cells negatively regulate monocyte activation argues that CD20 mAb-induced lymphoma depletion in wild type mice would be augmented by enhancing monocyte activation. Therefore, the effects of toll-like receptor (TLR) stimulation on TNF-α production by bone marrow CD11b$^+$ monocytes was evaluated. TLR3 (polyinosinic-polycytidylic acid; poly I:C), TLR4 (LPS), and TLR9 (CpG) agonists induced significant TNF-α production by monocytes (FIG. 4A) and higher levels of FcγRII/III expression by innate effector cells (FIG. 4B).

Figure 4C:
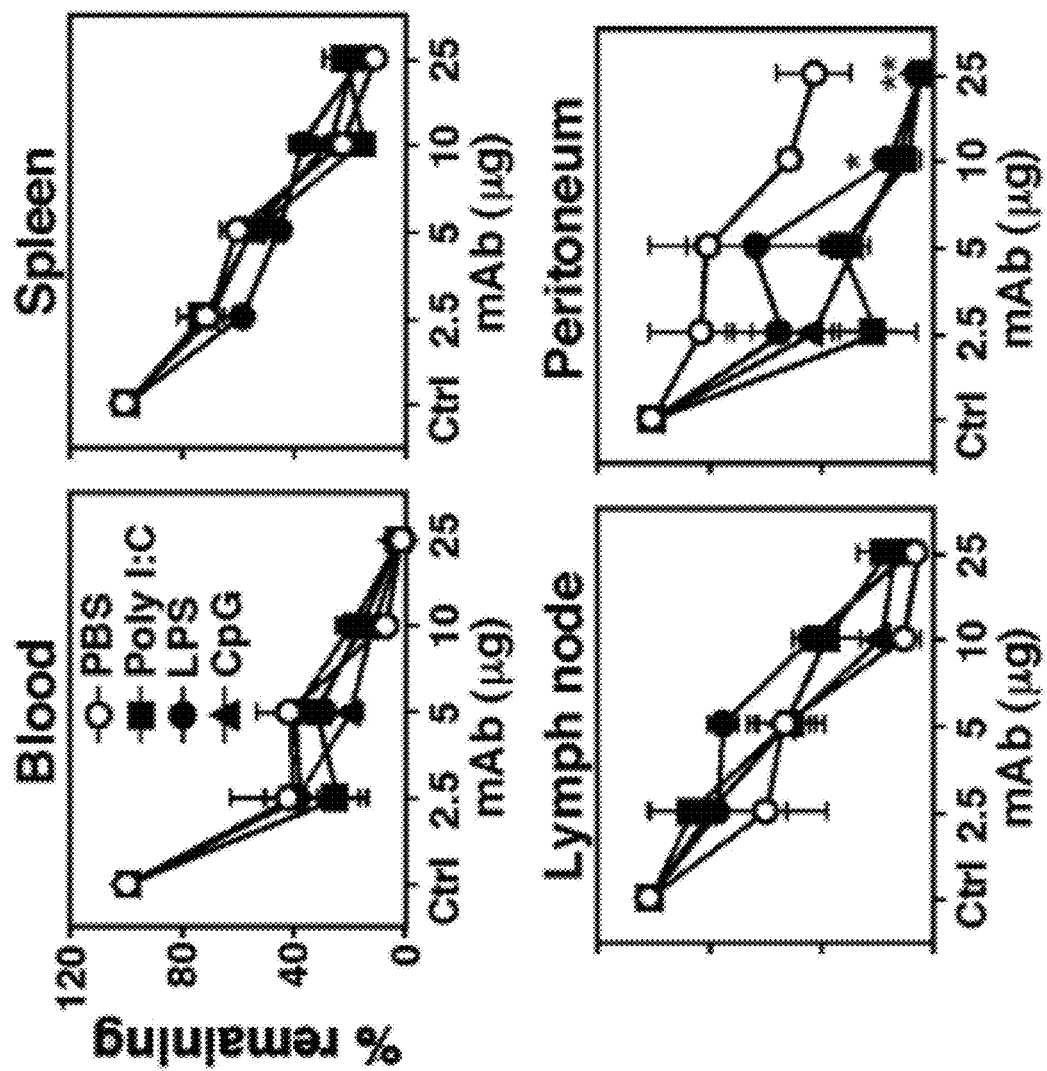
FIG. 4C (shows the effect of TLR agonists on endogenous B cell depletion by CD20 mAb in vivo. B cell depletion by CD20 mAb (2.5-250 μg) or isotype control (250 μg) mAb in mice given PBS (○), poly I:C (■), LPS (●), or CpG (▲). Values represent mean (±SEM) B220+ B cell numbers in CD20 versus control mAb-treated mice after 7 days (≥3 mice per value).
Figure 4D:
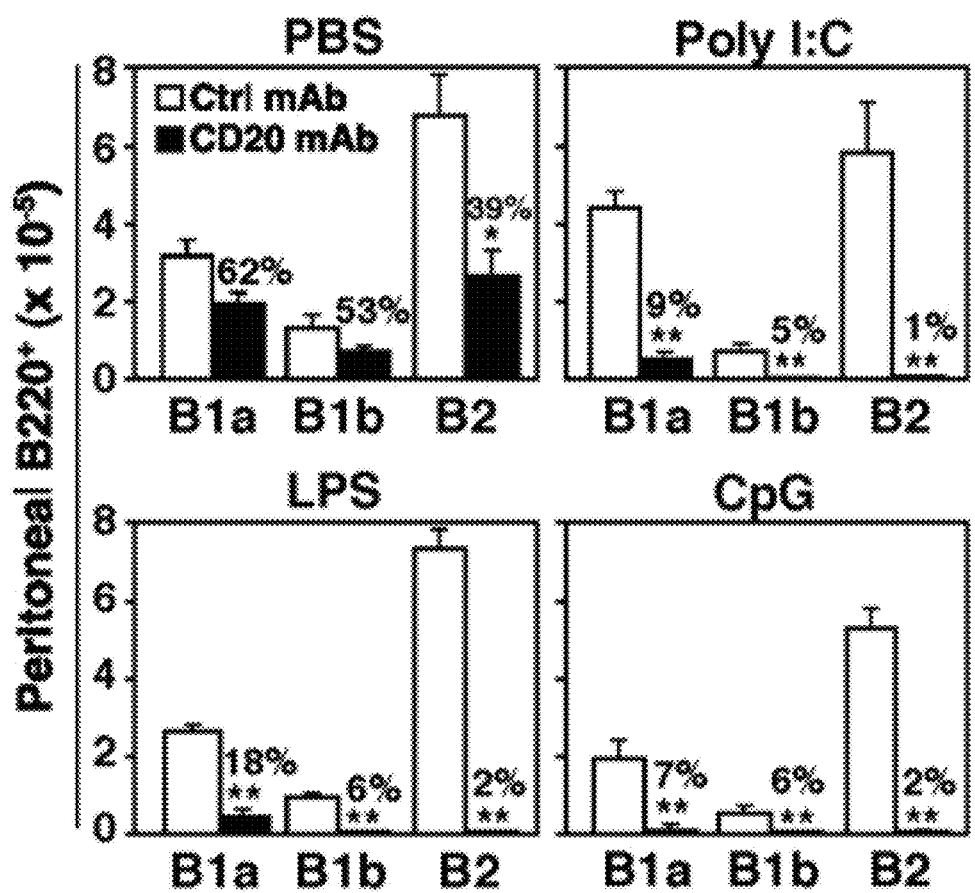
FIG. 4D shows peritoneal B1a (CD5+B220+), B1b (CD5$^-$CD11b+220$^-$), and B2 (CD5$^-$CD11b$^-$B220$^{hi}$) cell numbers (±SEM) 7 days after CD20 (filled bars) or control (open bars) mAb (25 μg) treatment of mice given PBS, poly I:C, LPS, or CpG (≥3 mice per value). B1b and B2 cells were distinguished based on their differential expression of CD11b.
Figure 4E:
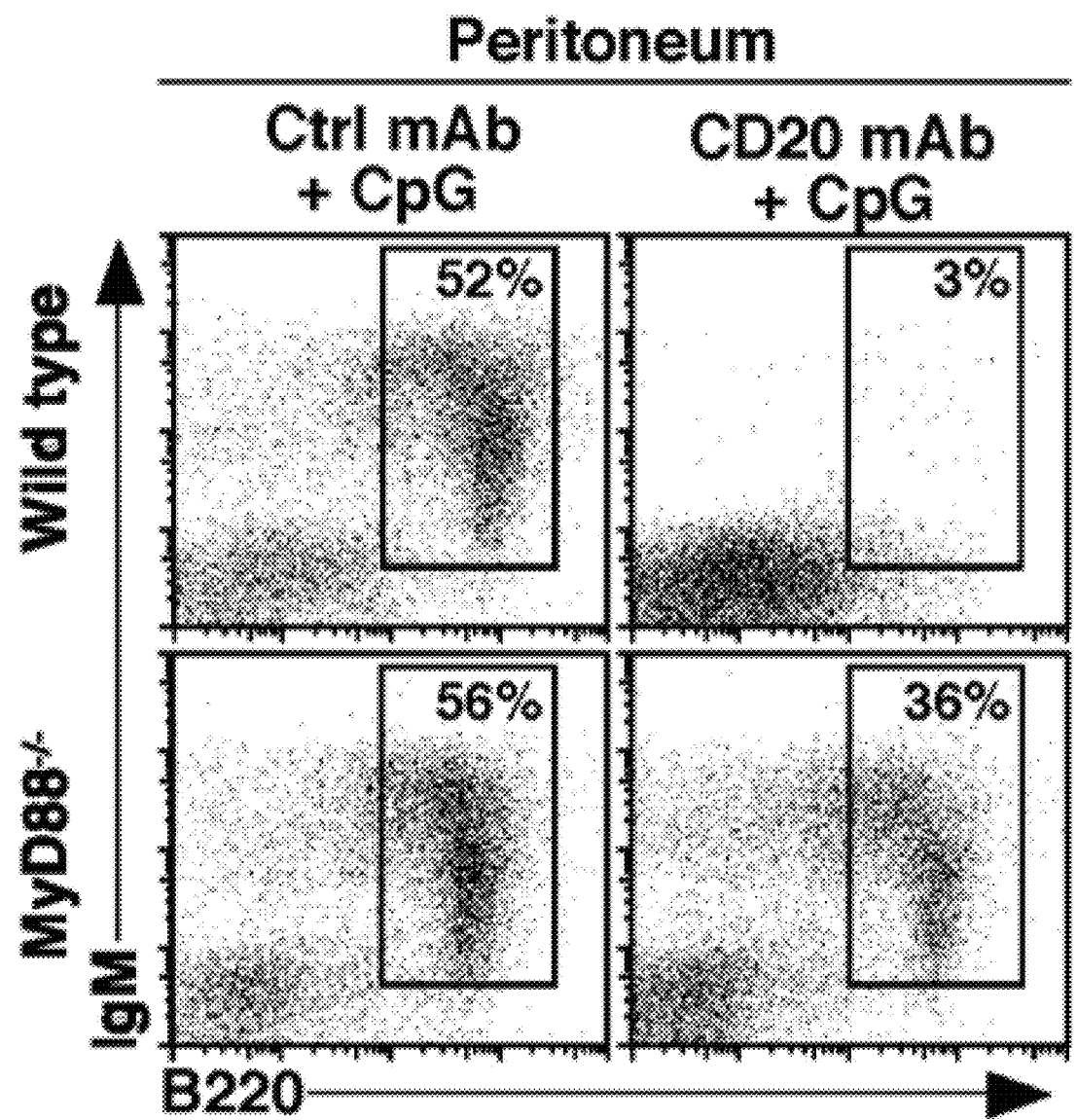
FIG. 4E shows that CpG treatment does not augment peritoneal B cell depletion by CD20 mAb in MyD88$^{-/-}$ mice. Representative peritoneal lymphocytes of CpG-treated MyD88$^{-/-}$ or wild type mice following CD20 or control mAb (25 μg) treatment. Percentages (±SEM) represent mean B220+ cell frequencies within the indicated gates 7 days after CD20 mAb treatment (≥3 mice per value) relative to control mAb-treated littermates (n=3).

Whether TLR agonists could augment B cell depletion was examined in mice given CD20 or control mAb (0-25 μg), with blood and tissue B cell numbers determined 7 days later. In control mice, CD20 mAb treatment depleted most circulating (>95%) B cells, and significantly reduced spleen and lymph node B cells in a dose-dependent manner (FIG. 4C). The concurrent treatment of mice with TLR agonists did not significantly enhance blood, spleen, or lymph node B cell depletion in mice given CD20 mAb. By contrast, TLR agonists significantly enhanced the removal of peritoneal B cells (FIG. 4C-D), which are normally protected from CD20 mAb-induced depletion (Hamaguchi et al., 2005). CD20 mAb treatment reduced the peritoneal CD5$^-$IgM$^{lo}$B220$^{hi}$ conventional B2 cell subset significantly, while peritoneal CD5$^+$CD11b$^+$IgM$^{hi}$B220$^{lo}$ B1a and CD5$^-$CD11b$^+$ IgM$^{hi}$B220$^{lo}$ B1b B cells were less affected (FIG. 4D). However, 98%, 82-93% and 94-95% of B2, B1a, and B1b cells, respectively, were depleted by CD20 mAb in mice given TLR agonists. Since the MyD88 adaptor protein is important for TLR signaling except for TLR-3 (Kawai et al., 1999; Laroux et al., 2005), B cell depletion was assessed in MyD88$^{-/-}$ and C57BL/6 mice treated with CD20 mAb plus CpG. The ability of CpG to enhance peritoneal B cell depletion by CD20 mAb was significantly reduced by MyD88-deficiency (FIG. 4E). Thus, TLR signaling significantly enhanced the effectiveness of CD20 mAb-induced B cell depletion.

Poly I:C Enhances CD20 mAb-Induced Lymphoma Depletion

Figure 5A:
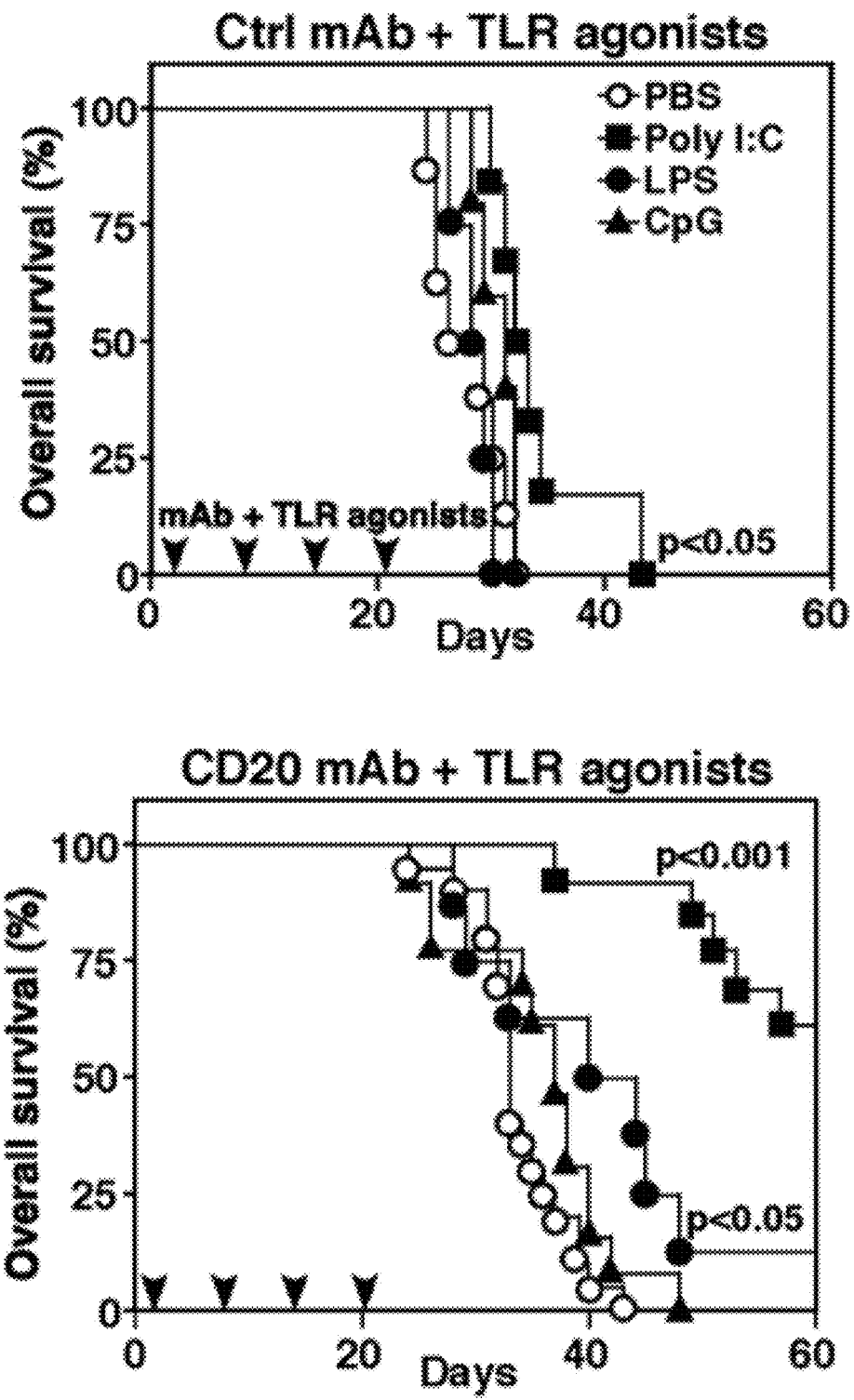
FIG. 5A shows that poly I:C, but not LPS or CpG, enhances CD20 mAb-induced lymphoma depletion. Control or CD20 mAb (10 μg) was given concurrently with PBS (○), poly I:C (■), LPS (●), or CpG (▲) on days 1, 7, 14, and 21 following 10$^5$ BL3750 cell transfers (4-20 mice per group). All mice that survived >60 days remained disease free for up to 6 months.
Figure 5B:
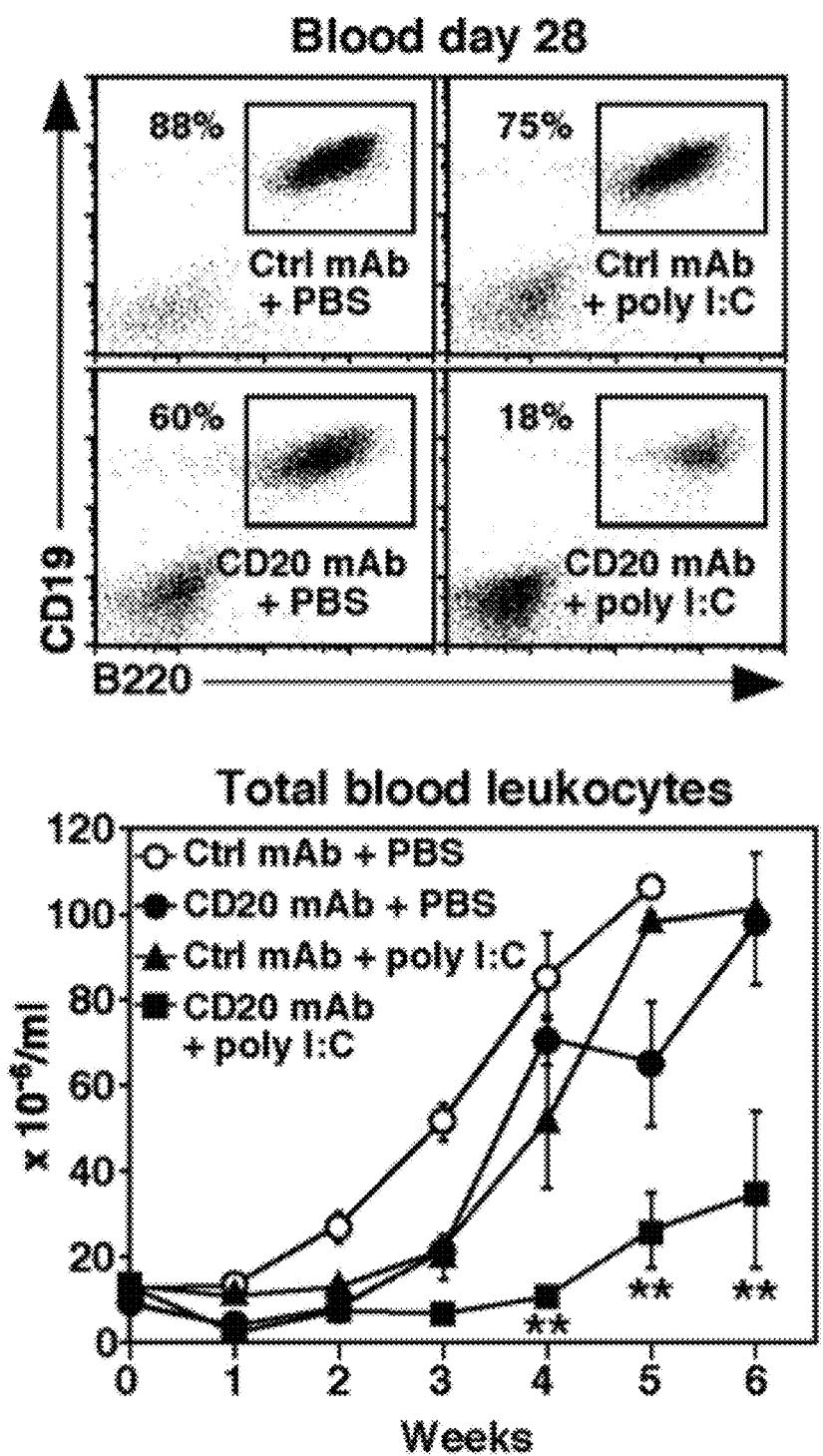
FIG. 5B shows that poly I:C enhances CD20 mAb-induced depletion of circulating tumor cells. Representative clearance of CD19+B220+ cells 28 days following treatment and BL3750 cell transfers for the mice shown in (A), with the relative frequencies of cells within the gates indicated. Line graphs indicate mean (SEM) blood leukocyte numbers.
Figure 5C:
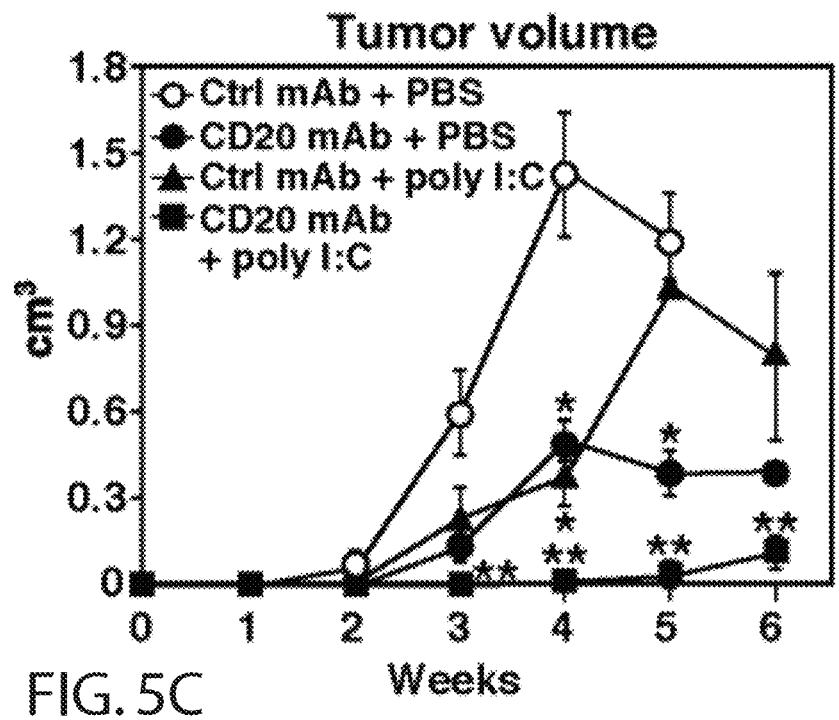
FIG. 5C shows the tumor volumes (±SEM) for the mice shown in FIG. 5A.
Figure 5D:
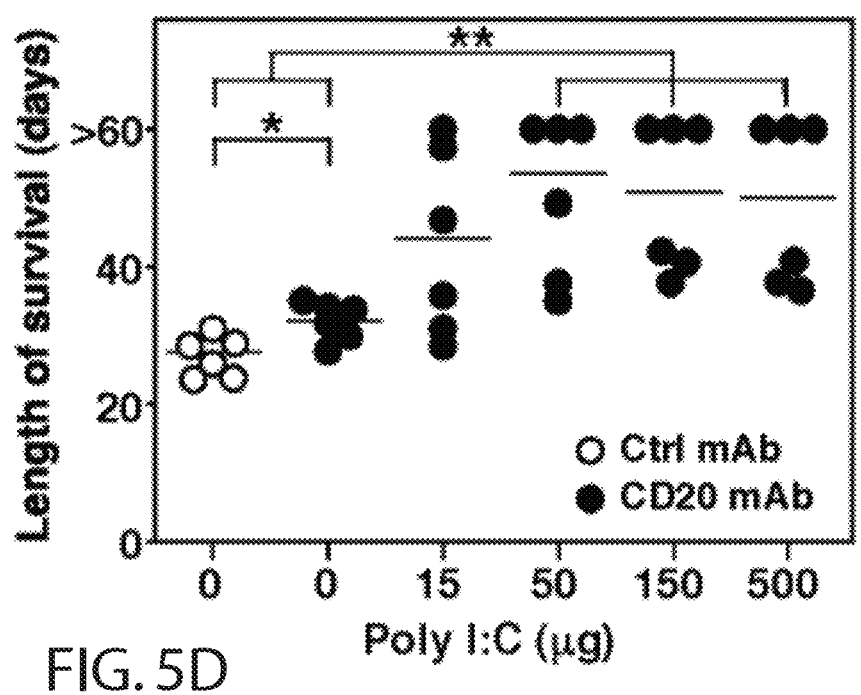
FIG. 5D shows the individual and mean (horizontal bars) mouse survival following BL3750 cell transfers with control (○) or CD20 mAb (●) plus poly I:C treatment over a range of concentrations (0-500 μg, 6 mice/group). All mice that survived >60 days remained disease free for up to 6 months.
Figure 5E:
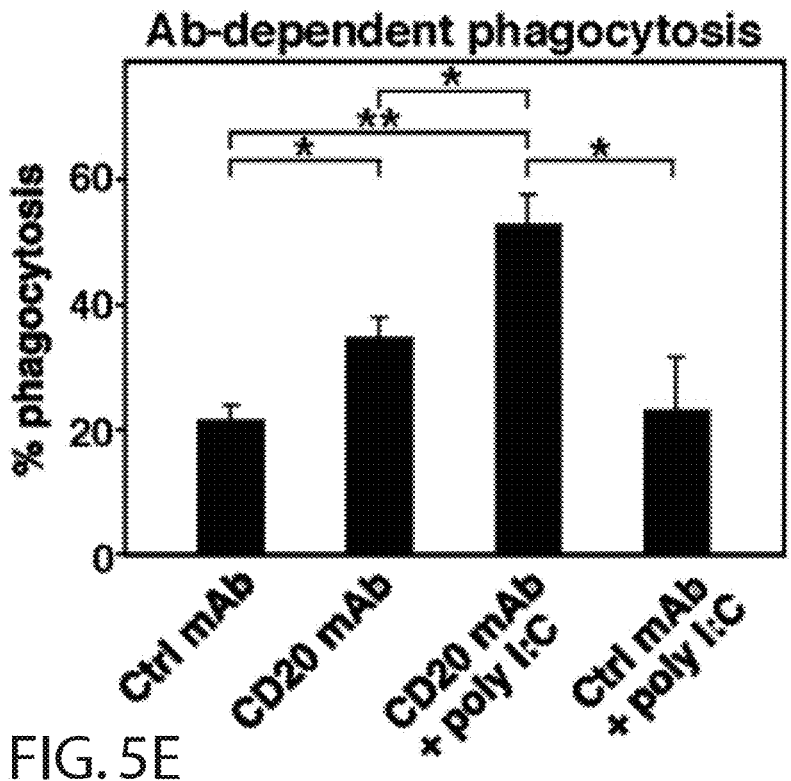
FIG. 5E shows that poly I:C enhances antibody-dependent monocyte phagocytosis of spleen B cells in vitro. Poly I:C-treated macrophages and CD20 mAb-coated CFSE-labeled B cells were mixed 1:1 and cultured for 2.5 h with B cell phagocytosis assessed by flow cytometry. Values indicate mean (±SEM) frequencies of monocytes containing CFSE-labeled B cells from 3-5 independent experiments.
Figure 5F:
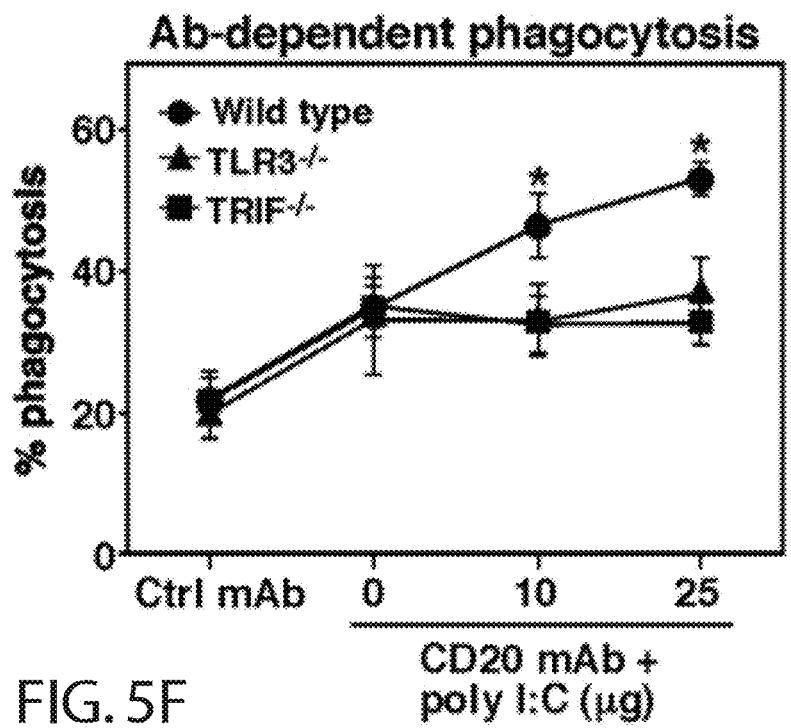
FIG. 5F shows that poly I:C induction of antibody-dependent B cell phagocytosis is TLR3- and TRIF-dependent. Macrophages from wild type, TLR3$^{-/-}$, or TRIF$^{-/-}$ mice were treated with poly I:C and incubated with CD20 mAb-coated B cells for 2.5 h, with antibody-dependent phagocytosis assessed by flow cytometry. Values indicate mean (±SEM) frequencies of monocytes containing CFSE-labeled B cells from 3-5 independent experiments.

The ability of TLR activation to augment lymphoma depletion was examined in mice given 10$^5$ BL3750 cells on day 0 followed by control mAb plus TLR agonists on days 1, 7, 14, and 21. Only poly I:C had a significant affect on mouse survival (median 33 days, FIG. 5A). The ability of TLR agonists to augment low dose CD20 mAb (10 μg) effectiveness in vivo was also examined. The median survival of mice given lymphomas and CD20 mAb alone was 33 days (range 24-43). However, the median survival of mice given CD20 mAb along with poly I:C was >60 days, with this treatment preventing tumors in 62% of mice for up to 6 months. The median survival of mice given CD20 mAb along with LPS (42 days) or CpG (37 days) was significantly less (p<0.001). The combination of low-dose CD20 mAb plus poly I:C also significantly reduced circulating leukocyte counts (p<0.01) and delayed tumor growth (p<0.01) when compared with CD20 mAb alone or control mAb plus poly I:C (FIG. 5B). Half of mice given 10$^5$ BL3750 cells along with low-dose CD20 mAb and 50-500 μg of poly I:C weekly for 4 weeks survived, while none of the control or CD20 mAb treated mice survived (p<0.01, FIG. 5D). In addition, poly I:C significantly enhanced macrophage phagocytosis of CD20 mAb-coated B cells in vitro in contrast to CD20 mAb alone or control mAb plus poly I:C (FIG. 5E). Poly I:C treatment was unable to augment the phagocytic capacity of macrophages isolated from TLR3$^{-/-}$ or TRIF$^{-/-}$ mice (FIG. 5F). Thus, poly I:C signaling through TLR3 and TRIF-dependent pathways was unique in its ability to augment CD20 mAb efficacy.

Poly I:C Activates Monocytes but not B10 Cells

Figure 6A:
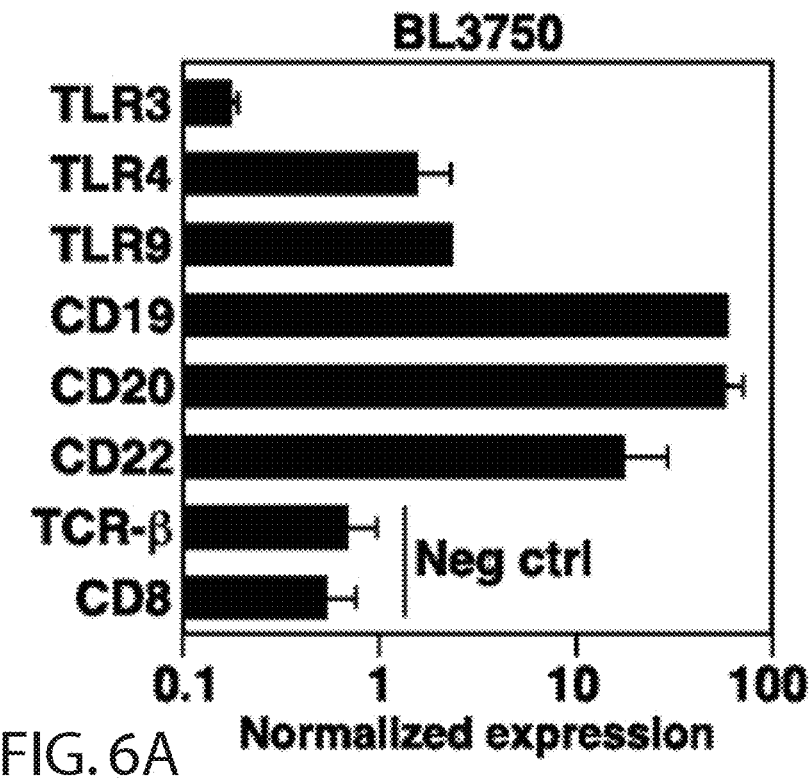
FIG. 6A shows that TLR gene expression by BL3750 cells assessed by gene chip analysis. Relative mean (±SEM) transcript levels are indicated.
Figure 6B:
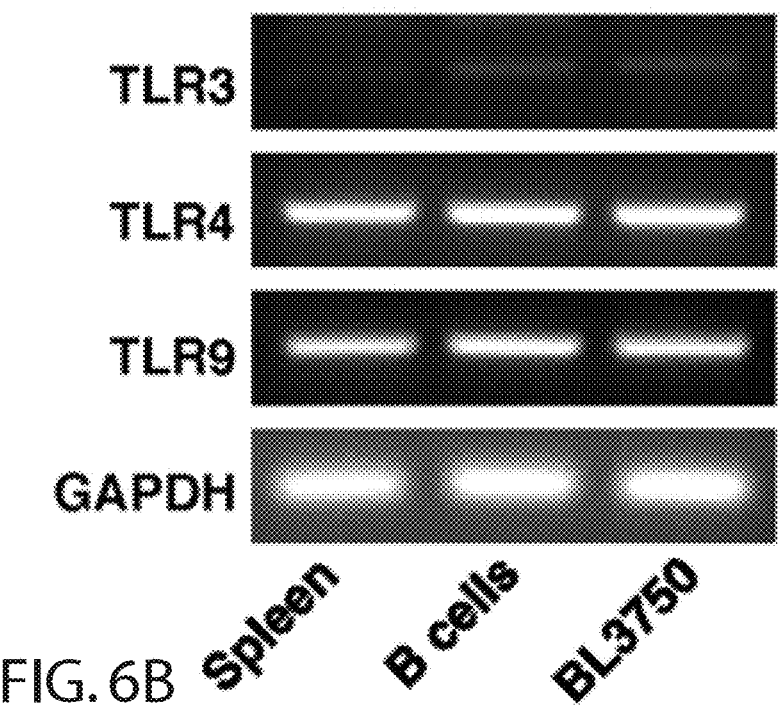
FIG. 6B shows TLR transcript expression by whole spleen, purified spleen B cells, and BL3750 cells. cDNA was PCR amplified using primer sets specific for mouse TLR3, TLR4, or TLR9, with GAPDH used as a positive control.
Figure 6C:
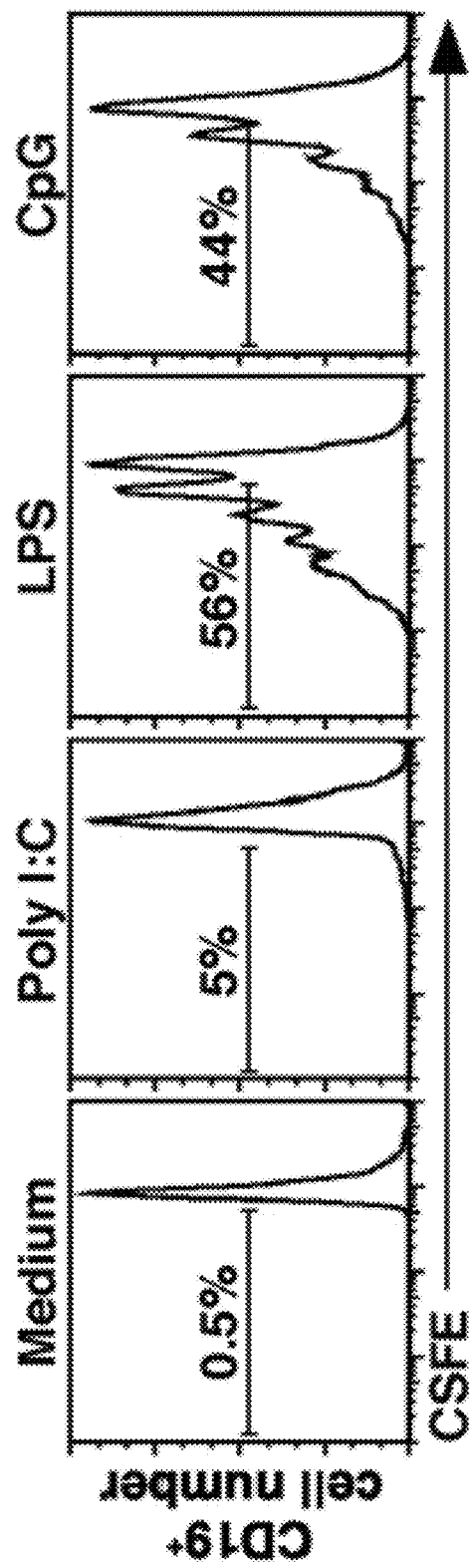
FIG. 6C shows that poly I:C does not induce B cell proliferation. Purified spleen B cells were CSFE-labeled and cultured with TLR agonists for 72 h. Representative frequencies of dividing $CD19^+$ cells are shown.
Figure 6D:
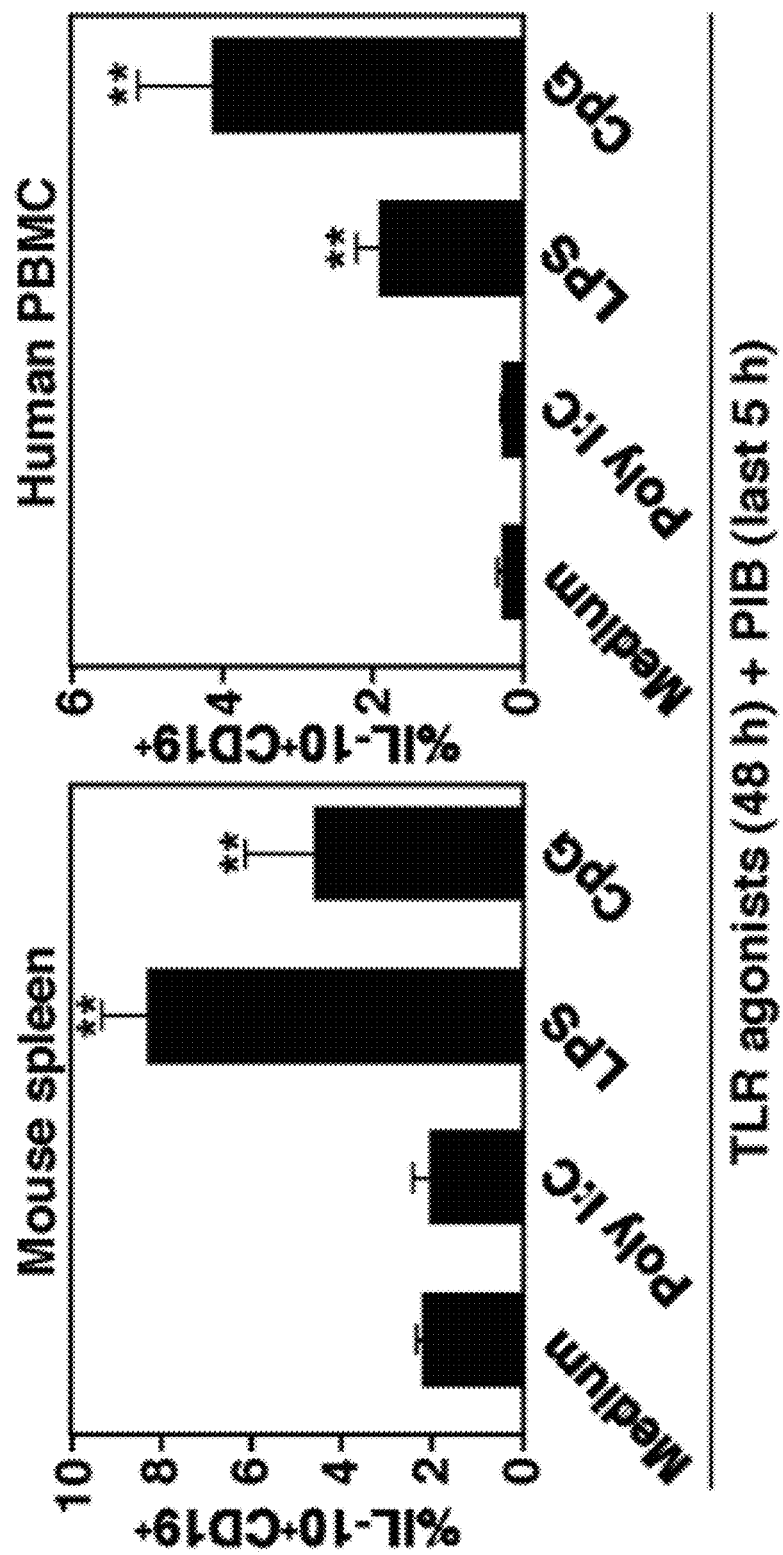
FIG. 6D shows that poly I:C does not induce mouse or human B10pro cell maturation. Mouse spleen (n=3-5/group) or human blood mononuclear (n=10-12/group) cells were stimulated for 48 h with LPS, CpG or poly I:C with PMA, ionomycin and brefeldin A (PIB) added for the last 5 h of culture. Bar graphs indicate frequencies of $IL10^+$ B cells assessed by flow cytometry.
Figure 6E:
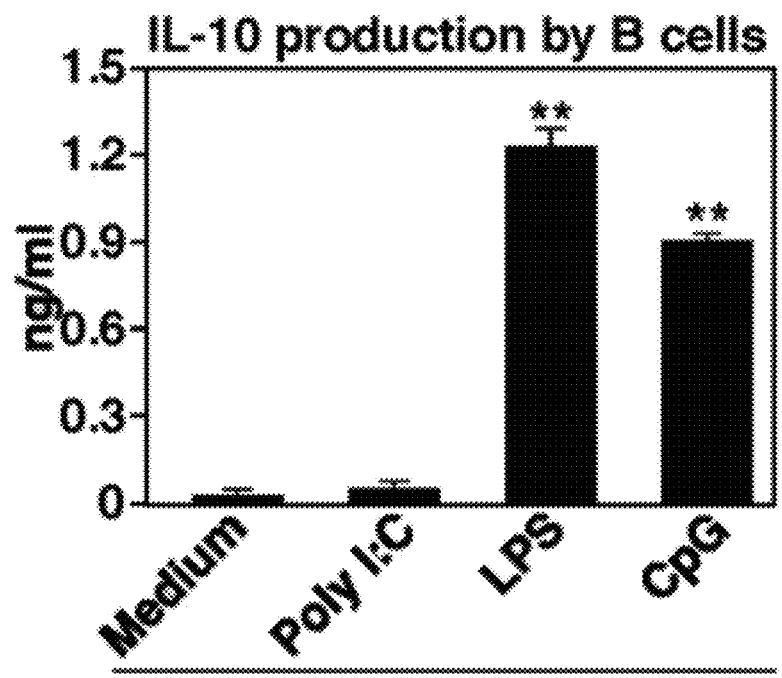
FIG. 6E shows that poly I:C does not induce B cell IL-10 production. Purified spleen B cells were cultured with TLR agonists for 72 h. Culture supernatant fluid IL-10 concentrations were quantified by ELISA.
Figure 6F:
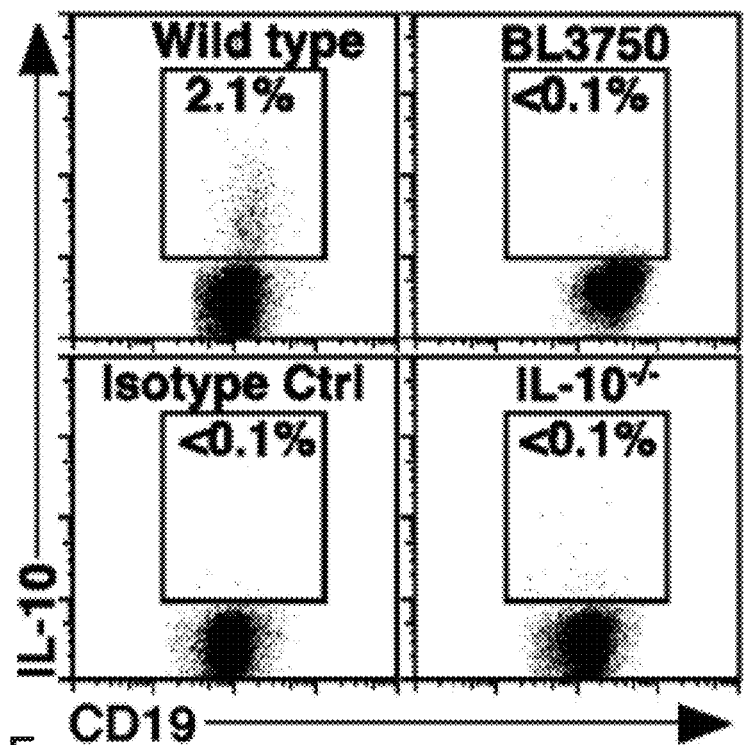
FIG. 6F shows that BL3750 cells do not express IL-10. BL3750 cells, wild type, or $IL-10^{-/-}$ mouse splenocytes were stimulated in vitro for 5 h to visualize IL-10 competent cells. Representative frequencies of IL-10-producing B cells are shown.

Whether poly I:C, LPS, or CpG differentially enhance CD20 mAb-induced lymphoma depletion by stimulating BL3750 cells, B cells, or B10 cells was assessed. First, BL3750 and spleen B cells expressed modest if any TLR3 transcripts, while TLR4 and TLR9 transcripts were readily identified (FIG. 6A-B). Consistent with this, purified spleen B cells proliferated significantly in response to LPS and CpG stimulation, while B cells cultured in medium alone or with poly I:C did not proliferate (p<0.05; FIG. 6C). Furthermore, culturing purified mouse spleen B cells or human blood mononuclear cells with LPS or CpG induced significant numbers of B10pro cells to mature into IL-10-competent B10 cells, while poly I:C was without effect (FIG. 6D). Culturing purified mouse spleen B cells with LPS or CpG also induced IL-10 secretion, while media alone or poly I:C stimulation were without effect (FIG. 6E). Furthermore, BL3750 cells were not induced to express IL-10 (FIG. 6F). Thus, poly I:C induces monocyte activation but does not induce B10 cell activation, IL-10 production, or clonal expansion.

Figure 7A:
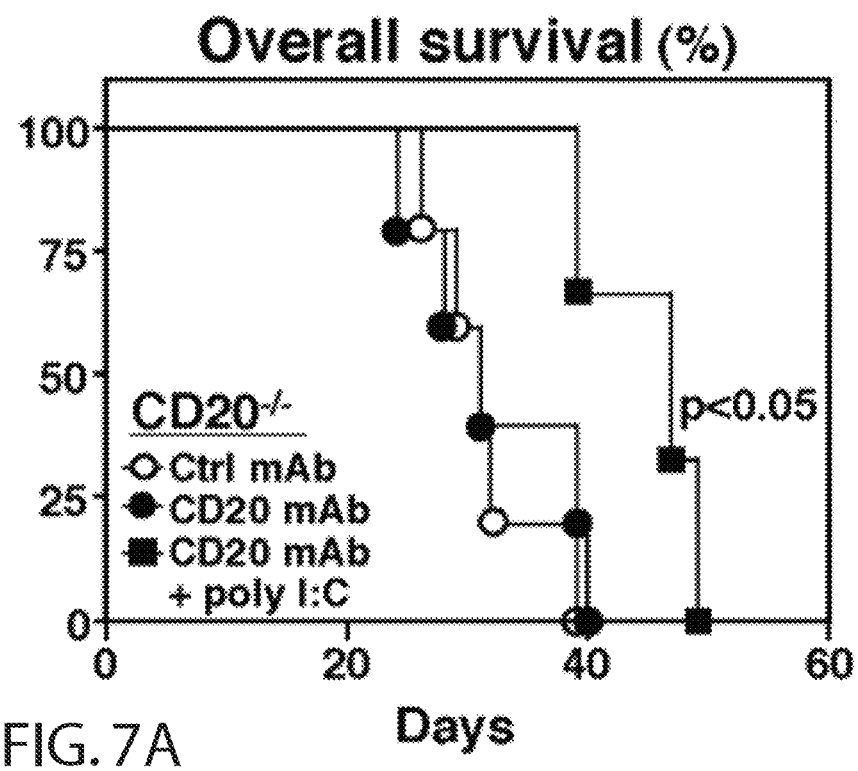
FIG. 7A is a graph showing that poly I:C enhances CD20 mAb efficacy in $CD20^{-/-}$ mice. Mouse survival following BL3750 cell ($10^6$ cells/mouse) transfers before mAb treatment is shown (3-5 mice per group).

Poly I:C Overcomes the Inhibitory Effect of Endogenous B Cells on CD20 Immunotherapy That poly I:C circumvents the negative regulatory effects of B10 cells was suggested by the ability of TLR3 stimulation to enhance monocyte phagocytic capacity without inducing B10 cell expansion or IL-10 production. To test this hypothesis, $CD20^{-/-}$ mice given $10^6$ BL3750 cells were subsequently treated with CD20 mAb plus poly I:C. While $CD20^{-/-}$ mice given CD20 mAb alone developed detectable tumors by 14-25 days, with a median survival of 31 days (range 24-40, FIG. 7A), CD20 mAb plus poly I:C treatment significantly delayed tumor growth and extended median survival to 47 days ($p<0.05$; FIG. 7A). Thus, poly I:C treatment reduced the inhibitory effect of endogenous B10 cells on CD20 immunotherapy.

Figure 7B:
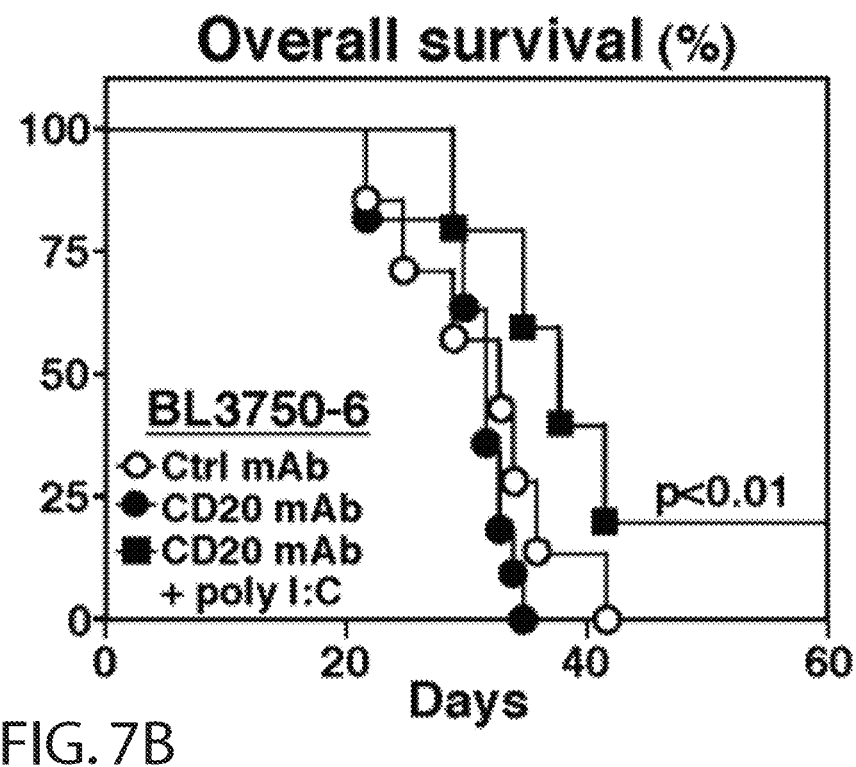
FIG. 7B is a graph showing that poly I:C enhances survival in wild type mice given $10^5$ CD20 mAb-resistant BL3750-6 lymphoma cells before mAb treatment (5-11 mice per group).

Whether poly I:C treatment could also overcome lymphoma resistance to CD20 mAb treatment was examined using a CD20 mAb-resistant CD20+ subclone of BL3750 cells. High dose CD20 mAb treatment (250 μg/mouse) given 1 day after the transfer of $10^5$ BL3750-6 cells had no therapeutic benefit, with median survival of 33 and 32 days in control or CD20 mAb treated mice, respectively (FIG. 7B). By contrast, CD20 mAb plus poly I:C treatment significantly ($p<0.01$) prolonged survival in wild type mice given BL3750-6 cells when compared with CD20 mAb treatment alone.

Figure 7C:
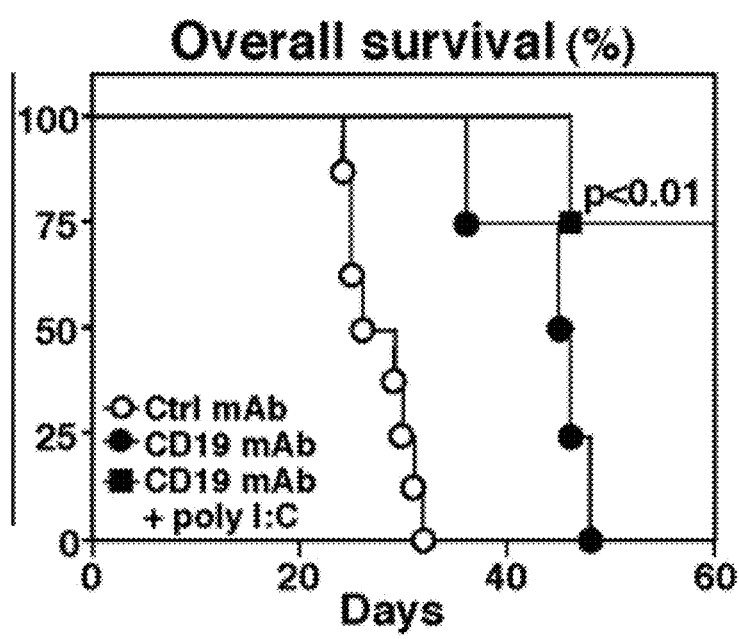
FIG. 7C is a graph showing that poly I:C enhances survival in wild type mice given $10^5$ BL3750 cells before CD19 mAb treatment (4-8 mice per group).

CD19 mAbs also deplete B cells in human CD19 transgenic mice through monocyte- and FcγR-dependent mechanisms. Therefore, the therapeutic benefit of poly I:C was also tested using a newly generated mouse anti-mouse CD19 mAb and BL3750 cells that express cell surface CD19 (Minard-Colin et al., 2008). CD19 mAb (100 μg/mouse) given 1 day after transfer of I:C BL3750 cells significantly enhanced mouse survival ($p<0.05$), with poly I:C plus CD19 mAb treatment significantly enhancing lymphoma depletion when compared with CD19 mAb treatment alone ($p<0.05$, FIG. 7C). Thereby, poly I:C treatment significantly enhanced both CD19 and CD20 mAb-induced lymphoma depletion in wild type mice.

References

Adachi, O., Kawai, T., Takeda, K., Matsumoto, M., Tsutsui, H., Sakagami, M., Nakanishi, K., and Akira, S. (1998). Targeted disruption of the MyD88 gene results in loss of IL-1 and IL-18-mediated function. Immunity 9, 143-150.

Dzhagalov, I., St John, A., and He, Y. W. (2007). The antiapoptotic protein Mcl-1 is essential for the survival of neutrophils but not macrophages. Blood 109, 1620-1626.

Edwards, A. D., Diebold, S. S., Slack, E. M., Tomizawa, H., Hemmi, H., Kaisho, T., Akira, S., and Reis e Sousa, C. (2003). Toll-like receptor expression in murine DC subsets: lack of TLR7 expression by CD8α DC correlates with unresponsiveness to imidazoquinolines. Eur J immunol 33, 827-833.

Hamaguchi, Y., Uchida, J., Cain, D. W., Venturi, G. M., Poe, J. C., Haas, K. M., and Tedder, T. F. (2005). The peritoneal cavity provides a protective niche for B1 and conventional B lymphocytes during anti-CD20 immunotherapy in mice. J Immunol 174, 4389-4399.

Hock, H., Hamblen, M. J., Rooke, H. M., Traver, D., Bronson, R. T., Cameron, S., and Orkin, S. H. (2003). Intrinsic requirement for zinc finger transcription factor Gfi-1 in neutrophil differentiation. Immunity 18, 109-120.

Kawai, T., Adachi, O., Ogawa, T., Takeda, K., and Akira, S. (1999). Unresponsiveness of MyD88-deficient mice to endotoxin. Immunity 11, 115-122.

Laroux, F. S., Romero, X. Wetzler, L., Engel, P. and Terhorst, C. (2005). Cutting edge: MyD88 controls phagocyte NADPH oxidase function and killing of gram-negative bacteria. J Immunol 175, 5596-5600.

Minard-Colin, V., Xiu, Y., Poe, J. C. Horikawa, M., Hamaguchi, Y., Haas, K. M., and Tedder, T. F. (2008). Lymphoma depletion during CD20 immunotherapy in mice is mediated by macrophage FcγRI, FcγRIII, and FcγRIV. Blood 112, 1205-1213.

Moore, K. W., de Waal Malefyt, R., Coffman. R. L. and O'Garra, A. (2001). Interleukin-10 and the interleukin-10 receptor. Annu Rev Immunol 19, 683-765.

Sato, S., Ono, N., Steeber, D. A., Pisetsky, D. S., and Tedder, T. F. (1996). CD19 regulates B lymphocyte signaling thresholds critical for the development of B-1 lineage cells and autoimmunity. J Immunol 157, 4371-4378.

Uchida, J., Hamaguchi, Y., Oliver, J. A., Ravetch, J. V., Poe, J. C., Haas, K. M., and Tedder, T. F. (2004a). The innate mononuclear phagocyte network depletes B lymphocytes through Fc receptor-dependent mechanisms during anti-CD20 antibody immunotherapy. J Exp Med 199, 1659-1669.

Uchida, J., Lee, Y., Hasegawa. M., Liang, Y., Bradney, A., Oliver, J. A., Bowen, K., Steeber, D. A., Haas, K. M., Poe, J. C., and Tedder, T. F. (2004b). Mouse CD20 expression and function. Int Immunol 16, 119-129.

Van Rooijen, N., and Sanders, A. (1994). Liposome mediated depletion of macrophages: mechanism of action, preparation of liposomes and applications. J Immunol Methods 174, 83-93.

Yanaba, K., Bouaziz, J.-D., Matsushita, T., Tasubata, T., and Tedder, T. F. (2009). The development and function of regulatory B cells expressing IL-10 (B10 cells) requires antigen receptor diversity and TLR signals. J Immunol 182, 7459-7472.

The invention claimed is:

1. A method of treating cancer in a subject comprising: administering a therapeutically effective amount of two active ingredients consisting of an antibody-based therapeutic agent useful for the treatment of the condition and a TLR3 agonist to a subject in need thereof, wherein the antibody-based therapeutic agent comprises an $F_c$gamma ($\gamma$) constant region and is specific for at least one of CD11a, CD19, CD20, TNF-$\alpha$, $\alpha$4 integrin, CD22, CD33, CD2, CD19, CD52, EGFR, or CD25.

2. The method of claim 1, wherein the TLR3 agonist is poly (I:C) or a poly I:C-like agent.

3. The method of claim 2, wherein the poly I:C-like agent is selected from poly-ICLC, poly I: poly $C_{12}$U and poly I: mercapto poly C.

4. The method of claim 1, wherein the antibody-based therapeutic agent mediates antibody-dependent cell-mediated cytotoxicity.

5. The method of claim 1, wherein the antibody-based therapeutic agent and the TLR3 agonist are administered concurrently.

6. The method of claim 1, wherein the antibody-based therapeutic agent is administered before or after the TLR3 agonist.

7. The method of claim 1, wherein the cancer is a solid, non-lymphoid tumor, or a tumor of epithelial origin.

8. The method of claim 1, wherein the cancer is selected from breast cancer, colorectal cancer, head and neck cancer, stomach cancer, renal cancer, lung cancer, ovarian cancer, prostate cancer, lymphoma, leukemia and brain cancer.

* * * * *